United States Patent
Amari et al.

(10) Patent No.: US 10,087,176 B2
(45) Date of Patent: *Oct. 2, 2018

(54) 3,5-DICHLORO,4-(3,4-(CYCLO-)ALKOXYPHENYL)--2-CARBONYLOXY)ETHYL)PYRIDINE DERIVATIVES AS PDE-4 INHIBITORS

(71) Applicant: Chiesi Farmaceutici S.p.A., Parma (IT)

(72) Inventors: Gabriele Amari, Parma (IT); Elisabetta Armani, Parma (IT); Mauro Riccaboni, Parma (IT); Andrea Rizzi, Parma (IT); Charles Baker-Glenn, Essex (GB); Wesley Blackaby, Essex (GB); Herve Van De Poel, Essex (GB); Ben Whittaker, Essex (GB)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/316,401

(22) PCT Filed: Jun. 4, 2014

(86) PCT No.: PCT/EP2014/061604
§ 371 (c)(1),
(2) Date: Dec. 5, 2016

(87) PCT Pub. No.: WO2015/185130
PCT Pub. Date: Dec. 10, 2015

(65) Prior Publication Data
US 2017/0152256 A1    Jun. 1, 2017

(51) Int. Cl.
*C07D 453/02*    (2006.01)

(52) U.S. Cl.
CPC .................. *C07D 453/02* (2013.01)

(58) Field of Classification Search
CPC ................................... C07D 453/02
See application file for complete search history.

(56) References Cited

FOREIGN PATENT DOCUMENTS

| EP | 2 022 783 | 2/2009 |
|---|---|---|
| WO | 2009/077068 | 6/2009 |
| WO | 2010/089107 | 8/2010 |
| WO | 2013/045280 | 4/2013 |

OTHER PUBLICATIONS

International Search Report in Application No. PCT/EP2014/061602 dated Jun. 4, 2014.

Odingo J O "Expert Opinion on Therapeutic Patents, Informa Healthcare, GB," vol. 15, No. 7 (2005) pp. 773-787.
U.S. Pat. No. 9,199,980, Dec. 1, 2015, US 2014-0155427, Armani, et al.
U.S. Pat. No. 9,090,606, Jul. 28, 2015, US 2014-0155428, Armani, et al.
U.S. Pat. No. 9,169,245, Oct. 27, 2015, US 2014-0155373, Armani, et al.
U.S. Pat. No. 9,133,185, Sep. 15, 2015, US 2015-0158858, Armani, et al.
U.S. Pat. No. 9,145,409, Sep. 29, 2015, US 2015-0158857, Armani, et al.
U.S. Appl. No. 15/316,312, filed Jun. 4, 2014, Armani, et al.
U.S. Appl. No. 14/723,964, filed May 28, 2015, US 2015-0352091, Armani, et al.
U.S. Pat. No. 9,326,976, May 3, 2016, US 2015-0352090, Armani, et al.
U.S. Appl. No. 15/148,225, filed May 6, 2016, US 2016-0326147, Armani, et al.
U.S. Pat. No. 9,636,336, May 2, 2017, US 2016-0346268, Armani, et al.
U.S. Pat. No. 9,597,323, Mar. 21, 2017, US 2016-0346260, Armani, et al.

*Primary Examiner* — Noble E Jarrell
*Assistant Examiner* — John S Kenyon
(74) *Attorney, Agent, or Firm* — Oblon, McClelland, Maier & Neustadt, L.L.P.

(57) ABSTRACT

The invention relates to novel 3,5-dichloro,4-(3,4-(cyclo-)alkoxyphenyl)-2-carbonyloxy)ethyl)pyridine compounds which are inhibitors of the phosphodiesterase 4 (PDE4) enzyme and muscarinic M3 receptor antagonists, methods of preparing such compounds, compositions containing them and therapeutic use thereof.

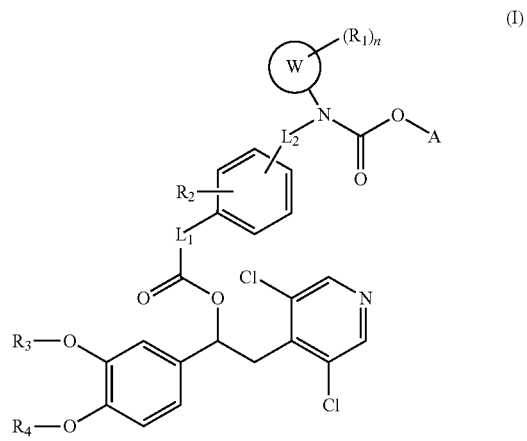

6 Claims, No Drawings

US 10,087,176 B2

3,5-DICHLORO,4-(3,4-(CYCLO-) ALKOXYPHENYL)–2-CARBONYLOXY) ETHYL)PYRIDINE DERIVATIVES AS PDE-4 INHIBITORS

FIELD OF THE INVENTION

The present invention relates to novel compounds which are both inhibitors of the phosphodiesterase 4 (PDE4) enzyme and muscarinic M3 receptor antagonists. More particularly, the invention relates to compounds of formula (I) as below described, methods of preparing such compounds, compositions containing them and therapeutic use thereof.

BACKGROUND OF THE INVENTION

Chronic obstructive pulmonary disease (COPD) is a respiratory disorder characterized by progressive, not fully reversible, airflow limitation associated with an abnormal pulmonary inflammatory response to noxious particles or gases.

For this reason, bronchial relaxation and inflammatory response suppression represent a mechanistic approach to the treatment of COPD that might improve symptoms such as dyspnea, wheezing, chest tightness, cough and mucus secretion, improve health status and reduce exacerbations.

Nowadays, the drug therapy options for COPD fall into 2 general classes: bronchodilators, (β2-adrenoceptor agonists, antimuscarinic agents and methylxanthines) and antiinflammatory agents (glucocorticosteroids and selective phosphodiesterase-4 (PDE4) inhibitors).

Bronchodilator drugs are the current mainstay of treatment for symptoms' relief.

As anticholinergic bronchodilators, the efficacy of muscarinic M3 antagonists is based on the fact that the major reversible component of airflow narrowing in COPD patients is the increase of acetylcholine (ACh) released to airway smooth muscle, by the bronchial postganglionic vagal efferent in some pathological conditions. Therefore, compounds that antagonize the action of ACh at muscarinic receptors are able to counteract the bronchoconstriction and thus improve lung function in these patients.

Muscarinic antagonists block the effects of ACh at muscarinic receptors.

Currently, there are five known muscarinic receptor subtypes (M1-M5); human airway smooth muscle contains M1, M2 and M3 receptors. M1 receptors facilitate neurotransmission through parasympathetic ganglia and are weakly expressed on submucosal glands in human airways. The M2 receptors are located on the smooth-muscle fibers. Some studies have suggested a small role of M2 mediating the inhibition of airway smooth-muscle relaxation caused by adenylyl cyclase activation by compounds such as beta agonists. In addition, presynaptic M2 receptors are found on postganglionic parasympathetic nerves that project to airway smooth muscle and mucus-producing cells. These presynaptic M2 autoreceptors provide a negative feedback mechanism, which, when stimulated, inhibit further release of ACh. Postsynaptic M3 receptors are known to mediate both contraction of smooth muscle in the respiratory tract and mucus secretion, making them a major target for symptomatic relief of COPD. Consequently, in the airways, the major effects of muscarinic antagonists are bronchodilation and reduction of mucus secretion via blockage of ACh-induced effects in the parasympathetic nervous system.

Given the distribution of muscarinic receptors, systemically available agents that bind to muscarinic receptors outside of the respiratory tract have the potential to produce unwanted side effects such as tachycardia, dry mouth, urinary retention and constipation. Whereas dry mouth is the most common systemic anticholinergic side effect associated with the use of antimuscarinic antagonists as a result of the systemic blockade of M1 and M3 receptors the most potentially serious systemic effect is tachycardia, which results from the blockade of cardiac M2 receptors.

Inhaled anticholinergic antimuscarinic drugs approved for the treatment of COPD include ipratropium bromide (Atrovent®), oxitropium bromide (Oxivent®) and tiotropium bromide (Spiriva®). Both ipratropium and oxitropium are short-acting agents. In contrast, tiotropium bromide is the only long-acting antimuscarinic agent (LAMA) currently marketed for COPD, proved to be suitable for one-daily administration as a dry powder. Several others newer LAMAs are newly registered for the treatment of COPD, including aclidinium bromide and glycopyrrolate bromide, or are currently in phase III development, including umeclidinium.

Although bronchodilators are quite effective to improve symptoms, they do not address the underlying chronic inflammation or the changes in airway structure.

Standard treatment with glucocorticosteroids as antiinflammatory agents has demonstrated limited efficacy. However, among the antiinflammatory agents currently being developed, PDE4 inhibitors proved to be effective in attenuating the responses of various inflammatory cells, through their ability to elevate cAMP levels.

PDE4 is the predominant PDE expressed in neutrophils and T cells, suggesting that PDE4 inhibitors would be effective in controlling inflammation in COPD. Inhibition of PDE4 in inflammatory cells influences various specific responses, such as the production and/or release of pro-inflammatory mediators including cytokines and reactive oxygen species, with a well-documented efficacy in animal models mimicking certain aspects of asthma and COPD, as well as inflammatory bowel disease, atopic dermatitis, psoriasis and rheumatoid arthritis.

The selective PDE4 inhibitor, roflumilast (Daxas®) is an approved phosphodiesterase-4 inhibitor for the treatment of COPD associated with chronic bronchitis and a history of exacerbations. Roflumilast inhibits lung inflammation and emphysema in a smoking model of COPD in mice. In COPD patients, oral roflumilast given over 4 weeks significantly reduces the numbers of neutrophils (by 36%) and CXCL8 concentrations in sputum. In clinical trials roflumilast (500 mg once daily) given over 12 months improved lung function in COPD patients to a small extent but had little effect in reducing exacerbations or improving quality of life. More recently roflumilast has been shown to significantly improve FEV 1 (by approximately 50 ml) and reduce exacerbation (by about 15%) in patients with severe disease who have frequent exacerbations and mucus hypersecretion. Roflumilast provides clinical benefit when added to salmeterol or tiotropium and so may be used as an additional treatment in patients with severe disease.

However, the clinical utility of PDE4 inhibitors has so far been compromised by the occurrence of mechanism-associated side effects, including headache, nausea and emesis, which often limited the maximally tolerated dose. This problem could be overcome by inhaled delivery and designing compounds with a potentially more advantageous therapeutic window.

Since bronchial relaxation and inflammatory response suppression represent a mechanistic approach to the treatment of COPD, the combination of muscarinic M3 antagonism with selective PDE4 inhibition may lead to a new class of drugs, combining both bronchodilating and antiinflammatory properties in one molecule, which may open new perspectives in the management of COPD.

Our co-pending application n. PCT/EP2013/075526 and the present invention address the above mentioned need by providing such kind of compounds.

SUMMARY OF THE INVENTION

The present invention is directed to compounds acting as inhibitors of the phosphodiesterase 4 (PDE4) enzyme and as muscarinic M3 receptor antagonists falling within the scope of formula (I) of our co-pending application PCT/EP2013/075526 but not disclosed therein. The invention is also directed to methods of preparing said compounds, compositions containing them and therapeutic use thereof.

In particular the invention is directed to compounds of formula (I),

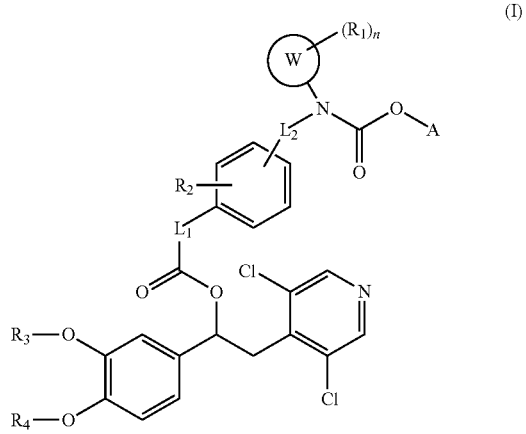

wherein
W is a substituted or unsubstituted phenyl;
$R_1$ is hydrogen or is independently selected in the group consisting of: methyl, hydroxyl, fluoro, methoxy, —CN, difluoromethyl, dimethylaminomethyl groups;
n is an integer ranging from 1 to 2;
$R_2$ is hydrogen;
$L_1$ is a bond;
$L_2$ is a group selected from —$(CH_2)_q$— wherein q is an integer ranging from 1 to 3;
$R_3$ and $R_4$ are both a methyl group;
A is a group represented by the formula (i):

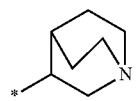

their N-oxides on the pyridine ring, deuterated derivative wherein at least one hydrogen atom is substituted by corresponding atoms of deuterium, and pharmaceutically acceptable salts and/or solvates thereof.

The term "pharmaceutically acceptable salts" refers to derivatives of compounds of formula (I) or of their corresponding N-oxides on the pyridine ring wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic acid residues such as carboxylic groups.

Cations of inorganic bases which can be suitably used to prepare salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid and citric acid.

The skilled persons will appreciate that many organic compounds can form complexes with solvents in which they are reacted or from which they are precipitated or crystallized. These complexes are known as "solvates" which are of further object of the invention. Polymorphs and crystalline forms of compounds of formula (I), of their N-oxides on the pyridine ring, or of pharmaceutically acceptable salts, or solvates thereof are a further object of the invention.

Hereinafter, compounds of formula (I), (I)', (IA), (Ia), (Ib), (Ic) and (Id), corresponding N-oxides on the pyridine ring, enantiomers, diastereoisomers and mixtures thereof, their pharmaceutically acceptable salts and solvates, and polymorphs or crystalline forms thereof defined in any aspect of the invention (except intermediate compounds described in the chemical processes) are referred to as "compounds of the invention".

The invention further comprises a process for the preparation of compounds of the invention.

The invention also provides pharmaceutical compositions of compounds of the invention either alone or in combination with another active ingredient, in admixture with one or more pharmaceutically acceptable carriers.

In a further aspect the invention provides the use of the compounds of the invention as a medicament.

In one aspect the invention provides the use of the compounds of the invention for the manufacture of a medicament.

In particular the invention provides the use of the compounds of the invention for the prevention and/or treatment of any disease wherein an inhibition of PDE4 activity along with muscarinic M3 receptor antagonism is desirable.

In particular the compounds of the invention alone or combined with other active ingredients may be administered for the prevention and/or treatment of a disease of the respiratory tract characterized by airway obstruction such as asthma and COPD. In one embodiment, the compounds of the invention may be administered for the prevention and/or treatment of COPD.

In a further aspect the invention provides the use of compounds of the invention for the preparation of a medicament for the prevention and/or treatment of any disease wherein an inhibition of PDE4 activity along with muscarinic M3 receptor antagonism is desirable.

Moreover the invention provides a method for prevention and/or treatment of any disease wherein an inhibition of PDE4 activity along with muscarinic M3 receptor antagonism is desirable, said method comprises administering to a patient in need of such treatment a therapeutically effective amount of a compound of the invention.

A further aspect of the invention provides a suitable inhalation device, comprising a pharmaceutical composition of a compound of the invention, which may be respectively selected from a single- or multi-dose dry powder inhaler, a pressurized metered dosed inhaler or a nebulizer and in particular a soft mist nebulizer.

A further aspect of the invention provides a kit comprising the pharmaceutical compositions of a compound of the invention either alone or in combination with one or more active ingredient and a device which may be a single- or multi-dose dry powder inhaler, a metered dose inhaler or a nebulizer.

DETAILED DESCRIPTION OF THE INVENTION

The invention is directed to a class of compounds acting both as inhibitors of the phosphodiesterase 4 (PDE4) enzyme and as muscarinic M3 receptor antagonists.

The invention relates to derivatives of general formula (I), N-oxides on the pyridine ring, deuterated derivatives and pharmaceutically acceptable salts and solvates thereof

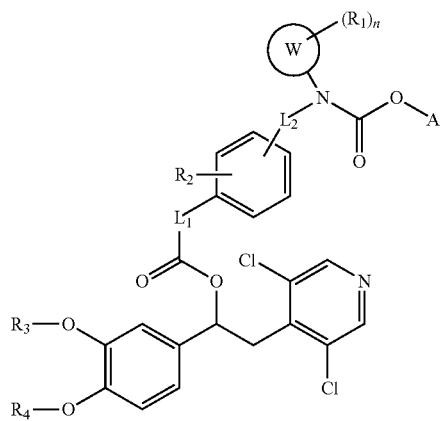

(I)

wherein $R_1$, $R_2$, $R_3$, $R_4$, A, W, $L_1$, $L_2$ and n are as defined above.

It will be apparent that compounds of general formula (I) at least contain one stereogenic center, namely represented by the carbon atom (1) and therefore exist as optical stereoisomers.

Where the compounds according to the invention have at least one stereogenic center, they may accordingly exist as enantiomers. Where the compounds according to the invention possess two or more stereogenic centers, they may additionally exist as diastereoisomers. All such isomers and mixtures thereof in any proportion are encompassed within the scope of the invention.

Preferably, the invention is directed to compounds of formula (I)', which are compounds of formula (I) as above defined where the absolute configuration of carbon (1) is that shown herebelow:

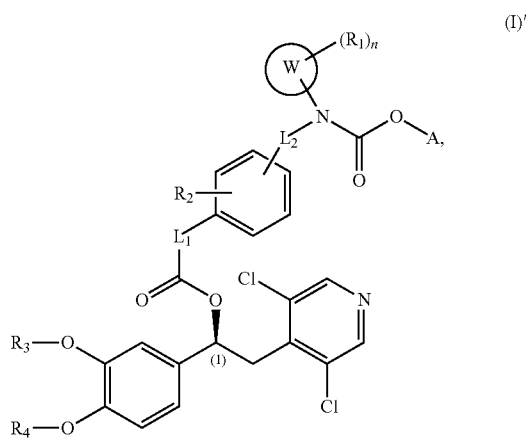

(I)'

The absolute configuration for carbon (1) is assigned on the basis of Cahn-Ingold-Prelog nomenclature based on groups' priorities.

In one preferred embodiment, for compounds of formula (I), absolute configuration at carbon (1) is (S).

The compounds of formula (I) possess a second stereogenic center, since A is a group of formula (i) as above defined, and then may exist as four diastereoisomers (Ia), (Ib), (Ic) and (Id) herebelow reported, which as single enantiomers, diastereoisomers or mixtures thereof are comprised within the scope of the invention:

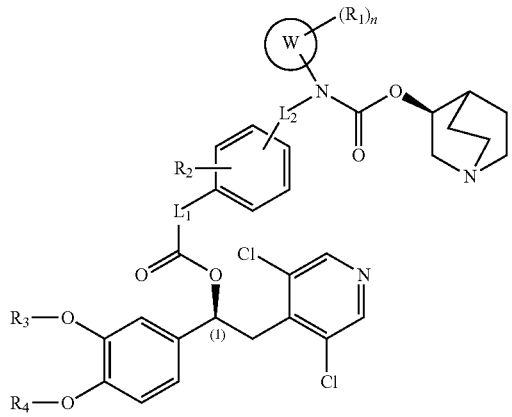

Ia

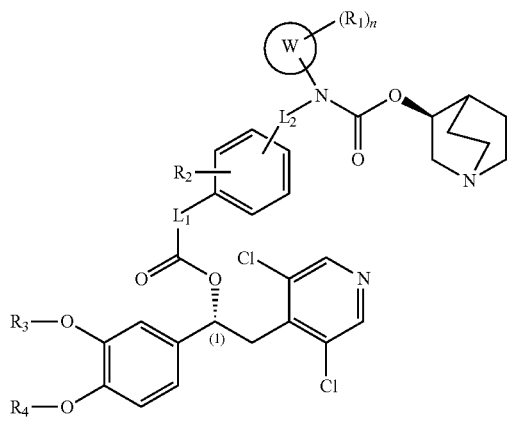

Ib

-continued

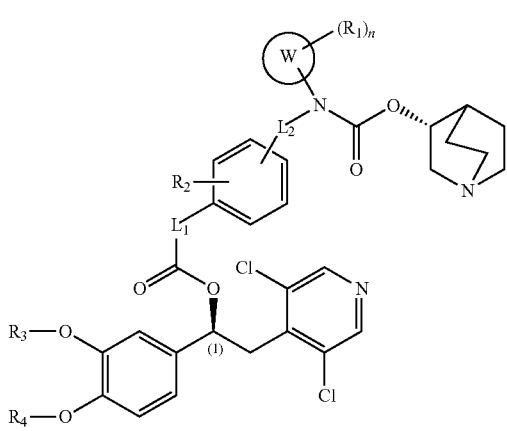

(Ic)

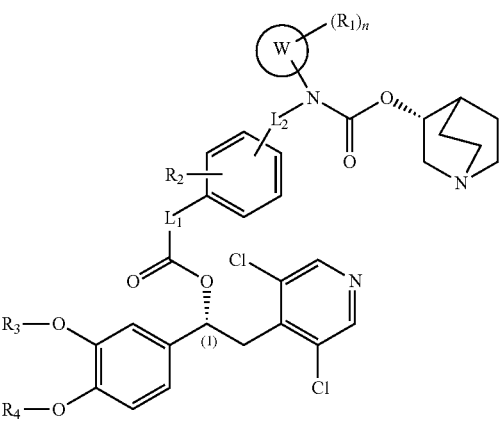

(Id)

In one embodiment, compounds of formula (Ic) are provided as above reported.

It is to be understood that all preferred groups or embodiments described herebelow and hereabove for compounds of formula (I) may be combined among each other and apply to compounds of formula (IA), (Ia), (Ib), (Ic), (Id) and (I)' as well mutatis mutandis.

Preferably, the invention provides compounds of formula (IA), which are N-oxides on the pyridine ring of compounds of formula (I), deuterated derivatives and pharmaceutically acceptable salts and solvate thereof:

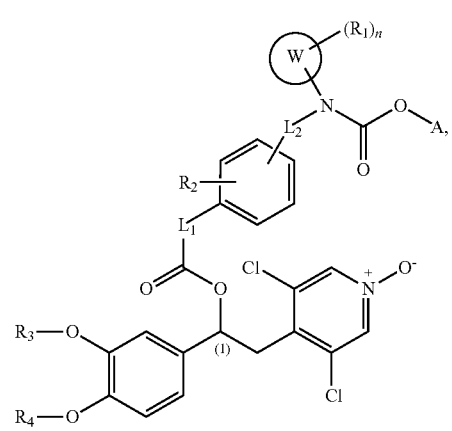

(IA)

wherein $R_1$, $R_2$, $R_3$, $R_4$, A, W, $L_1$, $L_2$, and n are as defined above.

The invention provides a compound selected from the group consisting of:

5  [(1S)-2-(3,5-dichloro-1-oxido-pyridin-1-ium-4-yl)-1-(3,4-dimethoxyphenyl)ethyl] 4-[(3-cyano-5-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl] 4-[(3-hydroxy-5-methyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl] 4-[(2,6-dihydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl] 4-[(2-fluoro-3-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl] 4-[3-(N-[(3R)-quinuclidin-3-yl]oxycarbonylanilino)propyl]benzoate;

[(1S)-2-(3,5-dichloro-1-oxido-pyridin-1-ium-4-yl)-1-(3,4-dimethoxyphenyl)ethyl] 3-[(2-hydroxy-5-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl] 3-[[2-(difluoromethyl)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl)ethyl]-4-[[2-(dimethylamino methyl)-N-[(3R)-quinuclidin-3-yl]oxycarbonyl-anilino] methyl]benzoate;

[(1S)-2-(3,5-dichloro-1-oxido-pyridin-1-ium-4-yl)-1-(3,4-dimethoxyphenyl)ethyl] 4-[3-(2-fluoro-N-[(3R)-quinuclidin-3-yl]oxycarbonyl-anilino)propyl]benzoate and pharmaceutically acceptable salts and/or solvates thereof.

The invention also provides processes for the preparation of compounds of the invention are provided.

Processes of preparation described below and reported in the following Schemes should not be viewed as limiting the scope of the synthetic methods available for the preparation of the compounds of the invention.

Compounds of formula (I) may be prepared according to schemes and procedures described in the co-pending international application PCT/EP2013/075526. In the following Schemes A and B, for compounds of formula (II) to (XIII), unless otherwise indicated, the groups $R_1$, $R_2$, $R_3$, $R_4$, A, $L_1$, $L_2$, W and n have the same meanings as described for compounds of formula (I) above. The group Y is part of the group $L_2$ above described for compounds of formula (I), and is a group —$(CH_2)_{q-1}$—, wherein q is an integer ranging from 1 to 3. The group X may be a leaving group such as I—, Br— or triflate ($CF_3SO_3$—).

In the following Schemes A and B compounds of formula (IA) are prepared starting from the pyridine N-oxides (VI) described in the co-pending international application n. PCT/EP2013/075526. Any corresponding compound of formula (I) which are not N-oxides on the pyridine ring may be similarly obtained starting from the non-oxidized pyridines, analogues of compounds (VI), described in the co-pending international application n. PCT/EP2013/075526.

In Scheme A reference is made to specific synthetic schemes (S1/A to S3/A), and in Scheme B reference is made to specific synthetic schemes (51/B to S5/B) which are better detailed in the following paragraphs.

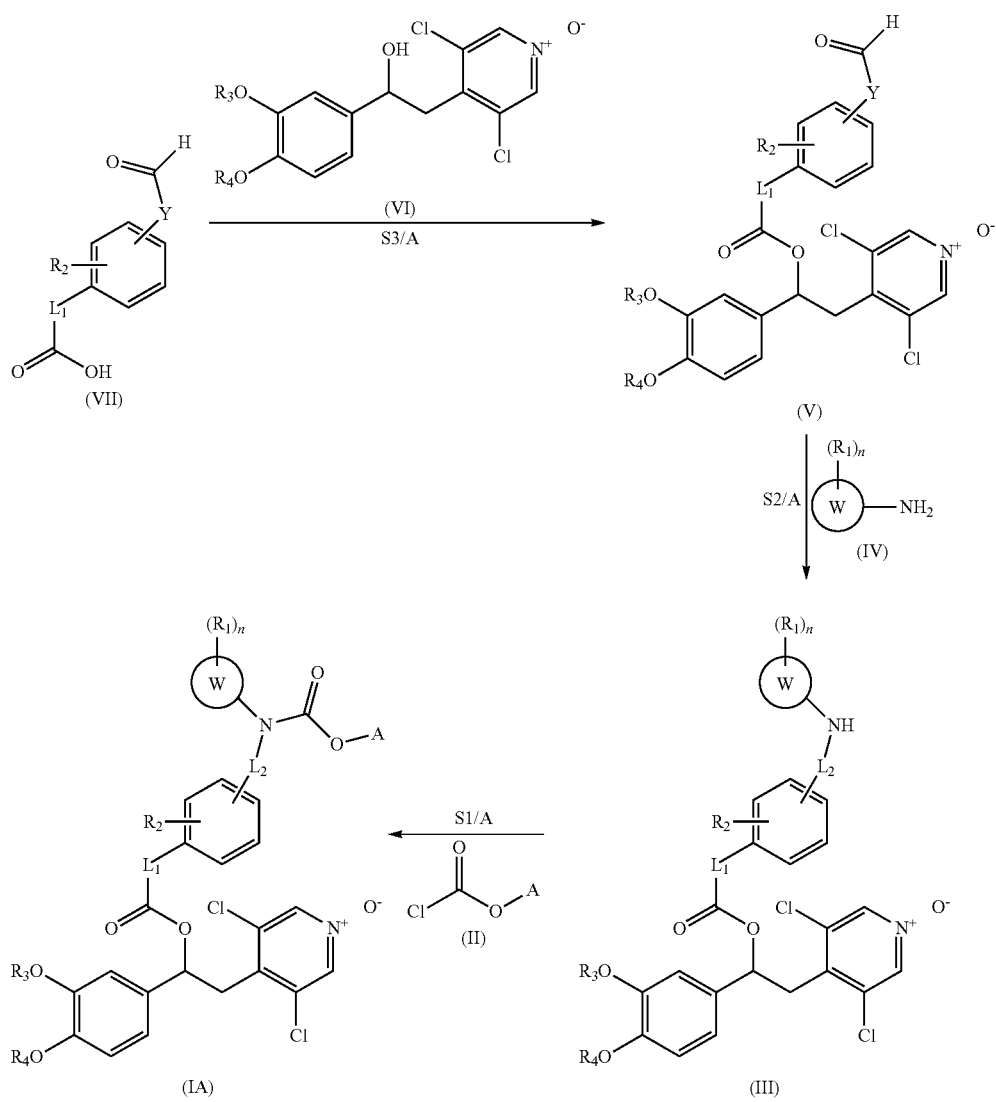

Scheme A

Compounds of formula (II) were prepared according to the process described below for Intermediate 1A (I-1 of the int. appl. PCT/EP2013/075526).

Compounds of formula (IV) were prepared according to the process described below for Intermediate 2A (I-32/A of the int. appl. CT/EP2013/075526).

Processes which can be used and are described in Scheme A should not be viewed as limiting the scope of the synthetic methods available for the preparation of the compounds of the invention.

In the following Schemes, for compounds of formula (II) to (VII), unless otherwise indicated, groups $R_1$, $R_2$, $R_3$, $R_4$, A, $L_1$, $L_2$, W and n have the same meanings as described for compounds of formula (I) above.

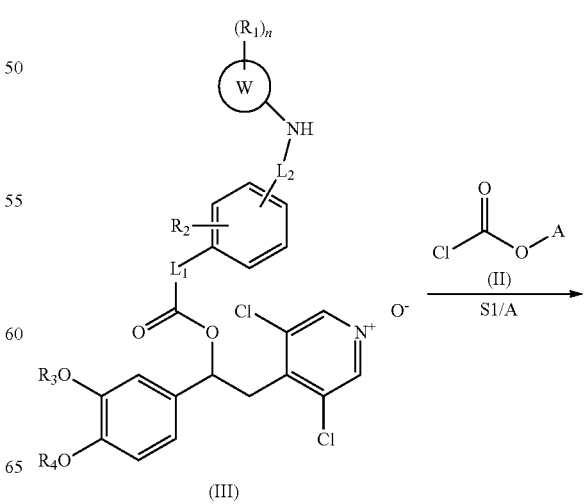

Scheme S1/A

-continued

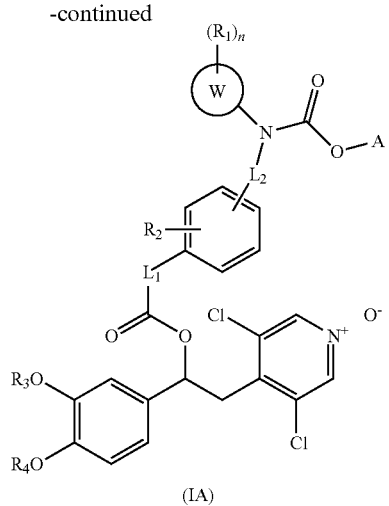

(IA)

Typical reaction conditions comprise reacting a compound of formula (III) with a compound of formula (II) in a suitable solvent, such as CH₃CN or pyridine, and an optional catalyst, such as DMAP, at an appropriate temperature such as room (or ambient) temperature or 0° C. to 100° C.

Compounds of formula (III) may be prepared according to Scheme S2/A by reaction of a compound of formula (V) with an appropriate compound of formula (IV) as below reported.

Scheme S2/A

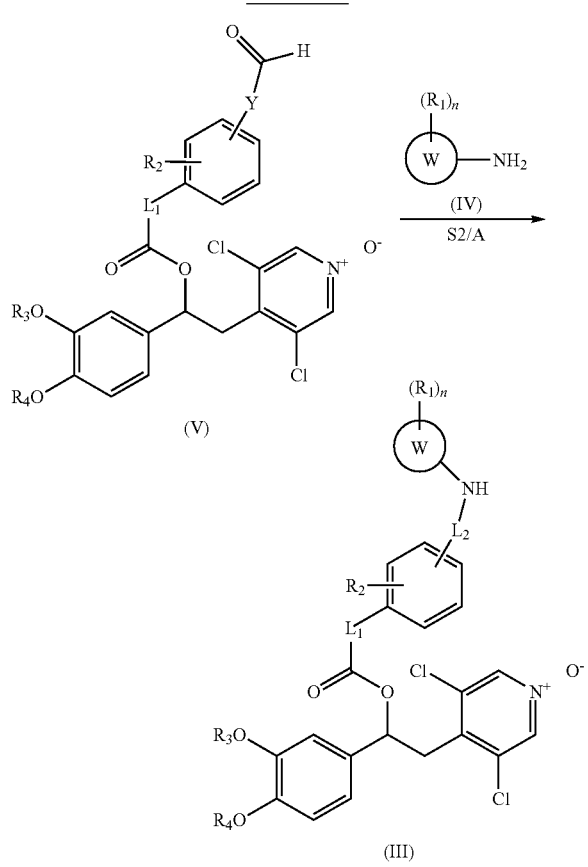

Typical reaction conditions comprise reacting a compound of formula (V) with a compound of formula (IV) in a suitable solvent, such as an alcoholic solvent or DCM or THF, in the presence of an acid, such as acetic acid, under reducing conditions, for example with sodium borohydride, sodium triacetoxyborohydride, sodium cyanoborohydride or by catalytic hydrogenation, and an optional catalyst, such as DMAP, at an appropriate temperature such as room (or ambient) temperature or 0° C. or 40° C. or 50° C.

Compounds of formula (V) may be prepared according to Scheme S3/A below by reaction of a compound of formula (VII) with a compound of formula (VI) as below reported.

Scheme S3/A

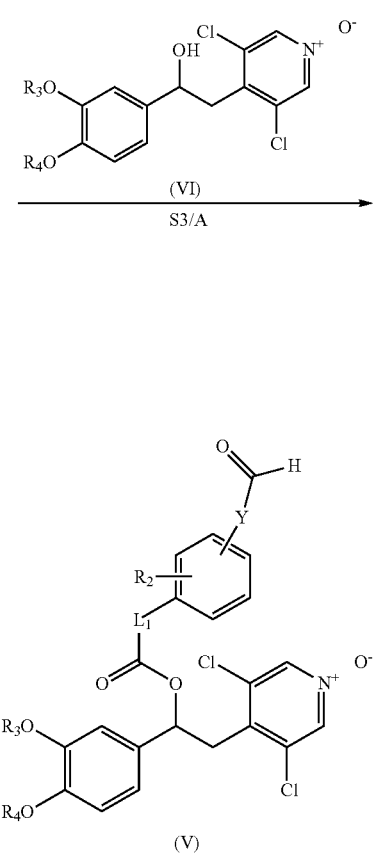

Typical reaction conditions comprise reacting a compound of formula (VII) with a compound of formula (VI) in a suitable solvent, such as DCM, in the presence of a coupling agent, such as EDC/DMAP or HATU, at an appropriate temperature such as room (or ambient) temperature or 40° C.

Compounds of formula (VI) were prepared as described in the co-pending international application n. PCT/EP2013/075526.

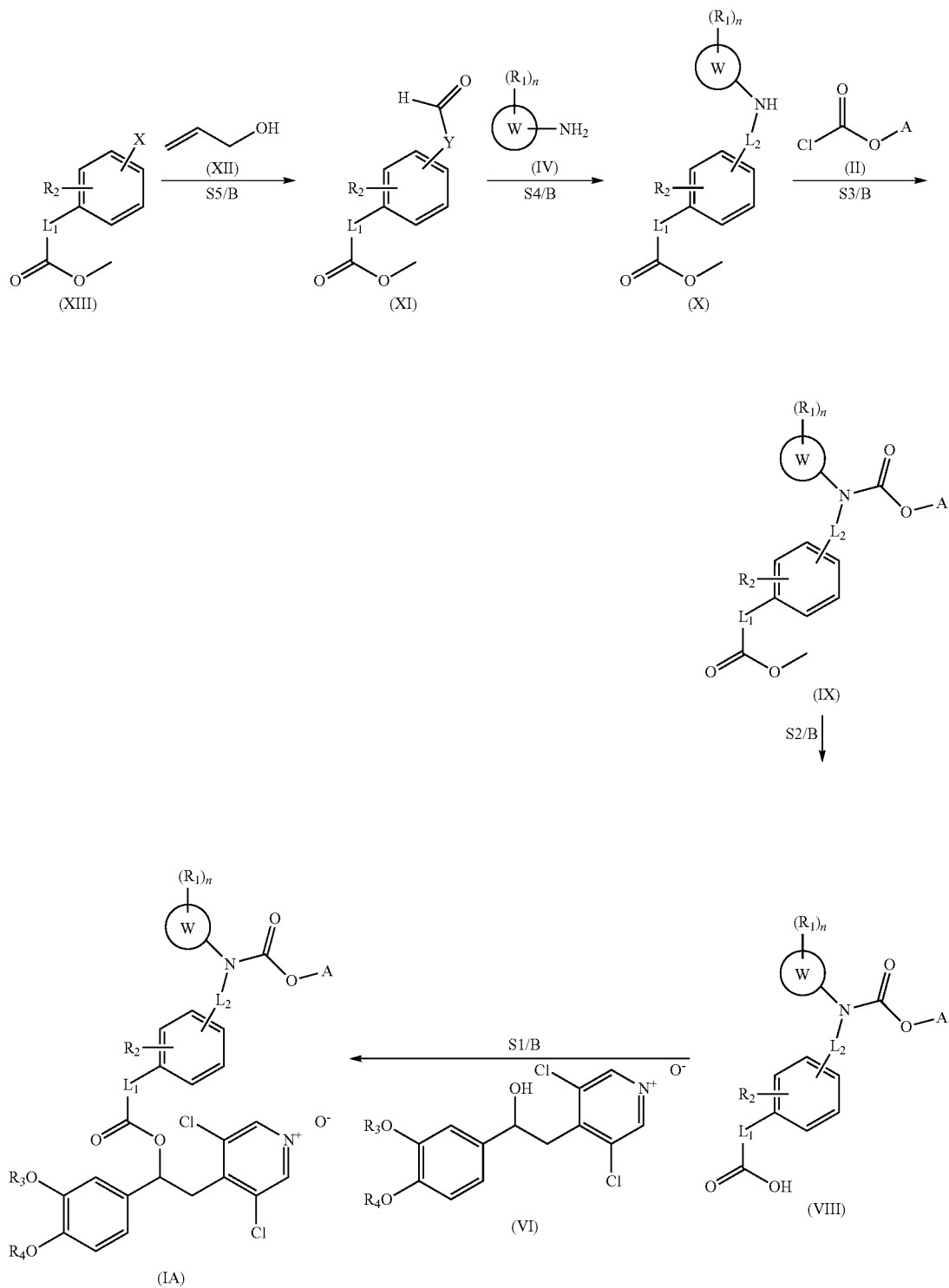

Scheme B

Processes which can be used and are described in Scheme B should not be viewed as limiting the scope of the synthetic methods available for the preparation of the compounds of the invention.

In the following Schemes, for compounds of formula (II), (IV), (VI), (VIII)-(XIII), unless otherwise indicated, groups $R_1$, $R_2$, $R_3$, $R_4$, A, $L_1$, $L_2$, W and n have the same meanings as described for compounds of formula (I) above.

Scheme S1/B

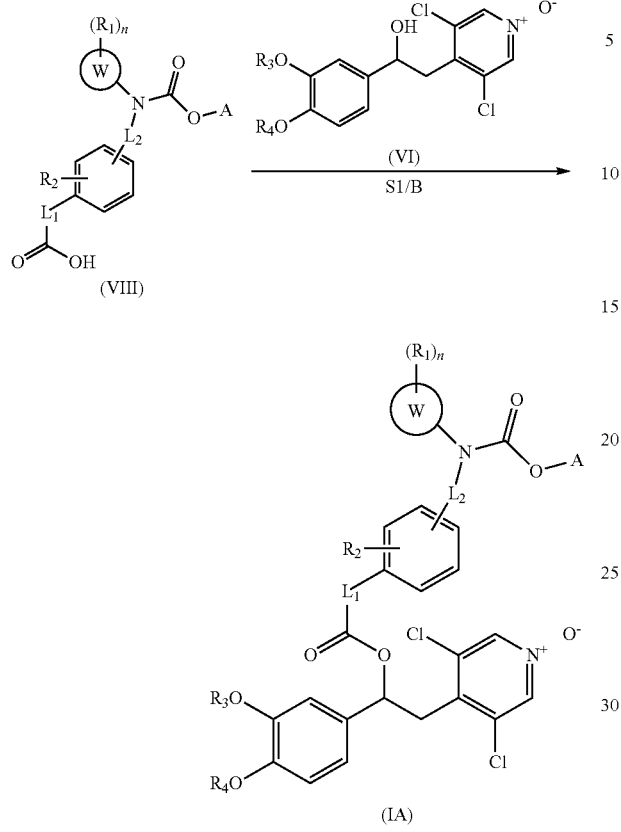

Typical reaction conditions comprise reacting a compound of formula (VIII) with a compound of formula (VI) in a suitable solvent, such as DCM, in the presence of a coupling agent, such as EDC/DMAP or HATU, at an appropriate temperature such as room (or ambient) temperature or 40° C.

Compounds of formula (VI) were prepared as described in the co-pending international application n. PCT/EP2013/075526

Compounds of formula (VIII) may be prepared according to Scheme S2/B below by reaction of a compound of formula (IX) as below reported.

Scheme S2/B

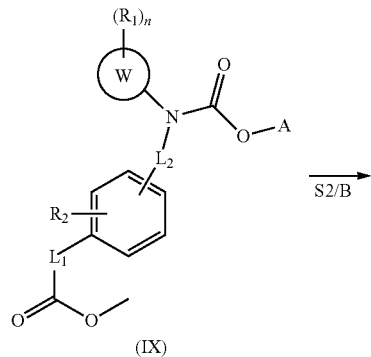

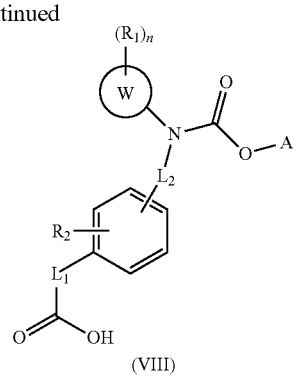

Typical reaction conditions comprise hydrolysis of a compound of formula (IX) in a suitable solvent mixture, such as THF/MeOH/water, in the presence of a suitable base, e.g. lithium hydroxide, at an appropriate temperature such as room temperature or 40° C.

Compounds of formula (IX) may be prepared according to Scheme S3/B below by reaction of a compound of formula (X) with a compound of formula (II) as below reported.

Scheme S3/B

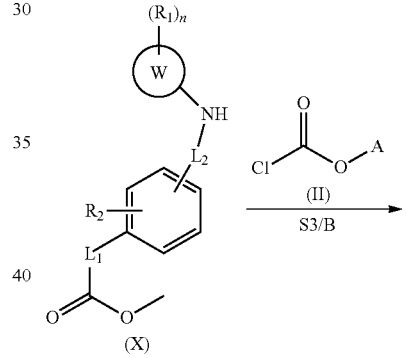

Typical reaction conditions comprise reacting a compound of formula (X) with a compound of formula (II) in a suitable solvent, such as $CH_3CN$ or pyridine, and an optional catalyst, such as DMAP, at an appropriate temperature such as room (or ambient) temperature or 0° C. to 100° C.

Compounds of formula (X) may be prepared according to Scheme 4/B (S4/B) by reaction of a compound of formula (XI) with an appropriate compound of formula (IV) as below reported.

Scheme S4/B

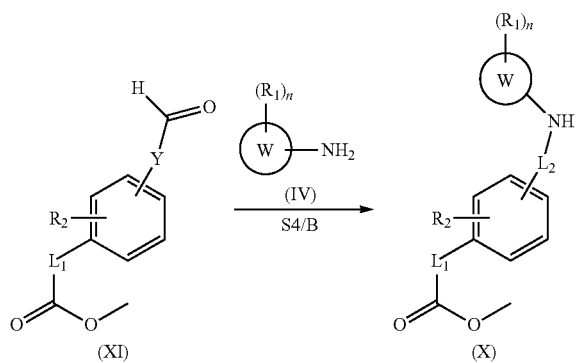

Typical reaction conditions comprise reacting a compound of formula (XI) with a compound of formula (IV) in a suitable solvent, such as an alcoholic solvent or DCM or THF, in the presence of an acid, such as acetic acid, under reducing conditions, for example with sodium borohydride, sodium triacetoxyborohydride, sodium cyanoborohydride or by catalytic hydrogenation, and an optional catalyst, such as DMAP, at an appropriate temperature such as room (or ambient) temperature or 0° C. or 40° C. or 50° C.

Compounds of formula (XI) may be prepared according to Scheme 5/B (S5/B) by reaction of a compound of formula (XIII) with an appropriate compound of formula (XII) as below reported.

Scheme S5/B

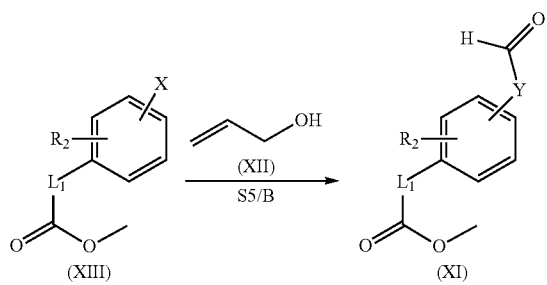

Typical reaction conditions comprise reacting a compound of formula (XIII) with a compound of formula (XII) in a suitable solvent, such as DMF, in the presence of a base, such as sodium bicarbonate or potassium carbonate, and in the presence of a palladium catalyst, such as Pd(OAc)$_2$, at an appropriate temperature, such as room (or ambient) temperature.

The processes described are particularly advantageous as they are susceptible of being properly modulated, through any proper variant known to the skilled person, so as to obtain any of the desired compounds of the invention. Such variants are comprised within the scope of the invention.

From all of the above, it should be clear that any of the described groups may be present as such or in any properly protected form.

In particular, functional groups present in the compounds of formula (II), to (XIII) and which could generate unwanted side reaction and by-products, need to be properly protected before the alkylation, acylation, coupling, oxidation or sulfonylation takes place. Likewise, subsequent deprotection of those same protected groups may follow upon completion of the said reactions.

In the invention, unless otherwise indicated, the term "protecting group" designates a protective group adapted to preserve the function of the group it is bound to. Typically, protecting groups are used to preserve amino, hydroxy, or carboxyl functions. Appropriate protecting groups may thus include, for example, benzyl, benzyloxycarbonyl, t-butoxycarbonyl, alkyl or benzyl esters or the like, which are well known [see, for a general reference, T. W. Green; Protective Groups in Organic Synthesis (Wiley, N.Y. 1999)].

Likewise, selective protection and deprotection of any of the said groups, for instance including carbonyl, hydroxy or amino groups, may be accomplished according to well known methods.

The N-oxides on the 4-pyridinyl ring of the compounds of formula (I) and embodiments thereof may be prepared according to methods available in the literature and well known to the skilled person. For instance they may be prepared by dissolving the compound of formula (I) or embodiments thereof in $CH_2Cl_2$ or $CHCl_3$, then adding an oxidizing agent such as m-chloro perbenzoic acid (mCPBA) to the resulting solution. Other oxidizing agents which may be used are hydrogen peroxide, perbenzoic acid, peracetic acid or potassium peroxymonosulfate (also known as Oxone).

Alternatively, in particular for those compounds comprising functional groups sensitive to oxidation, the corresponding N-oxides are prepared by carrying out the oxidation step before further functional groups are introduced, for example on compounds of formula (IX) as above reported.

In a preferred embodiment, the process for preparation of compounds of formula (I) or embodiments thereof is performed starting from N-oxide on the pyridine ring of compound of formula (II), thus allowing the preparation of compound of formula (I) or embodiments thereof in the form of N-oxides on the pyridine ring.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are within the ordinary knowledge of the skilled person.

From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

The invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y., U.S.A.

Administration of the compounds of the invention or may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the invention.

Various liquid oral dosage forms may also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known.

For topical administration the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metered aerosols or propellant-free inhalable formulations and may be administered through a suitable inhalation device which may be respectively selected from dry powder inhaler, pressurized metered dosed inhaler, or a nebulizer.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs) and mucus regulators.

The invention also provides combinations of a compound of the invention, with a β2-agonist selected from carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol and ASF-1020 and salts thereof.

The invention also provides combinations of a compound of the invention, with a corticosteroid selected from fluticasone propionate, fluticasone furoate, mometasone furoate, beclometasone dipropionate, ciclesonide, budesonide, GSK 685698, GSK 870086.

The invention also provides combinations of a compound of the invention, with an antimuscarinic agent selected from aclidinium, tiotropium, ipratropium, trospium, glycopyrronium and oxitropium salts.

The invention also provides combinations of a compound of the invention, with a PDE4 inhibitor selected from AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414 and RPL-554.

The present invention also provides combinations of a compound of the invention, with a P38 MAP kinase inhibitor selected from semapimod, talmapimod, pirfenidone, PH-797804, GSK-725, minokine and losmapimod and salts thereof.

Preferably, the invention provides combinations of a compound of the invention with an IKK2 inhibitor.

The invention also provides combinations of a compound of the invention with a HNE inhibitor selected from AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The invention also provides combinations of a compound of the invention with a leukotriene modulator selected from montelukast, zafirlukast and pranlukast.

The invention also provides combinations of a compound of the invention with a NSAID selected from ibuprofen and ketoprofen.

The invention also provides combinations of a compound of the invention with a mucus regulator selected from INS-37217, diquafosol, sibenadet, CS-003, talnetant, DNK-333, MSI-1956 and gefitinib.

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage comprised between 0.001 and 1000 mg/day, preferably between 0.1 and 500 mg/day.

When they are administered by inhalation route, the dosage of the compounds of the invention is advantageously comprised between 0.01 and 20 mg/day, preferably between 0.1 and 10 mg/day.

Preferably, the compounds of the invention alone or combined with other active ingredients may be administered for the prevention and/or treatment of any obstructive respiratory disease such as asthma, chronic bronchitis and chronic obstructive pulmonary disease (COPD).

However the compounds of the invention may be administered for the prevention and/or treatment of any disease wherein PDE4 inhibition or M3 antagonism is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, atherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular and wide-area pyodermias, endogenous and exogenous acne, acne rosacea, Behçet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolateroesclerosis (ALS), multiple systems atrophy (MSA), schizophrenia, Parkinson's disease, Huntington's disease, Pick's disease, depression, stroke, and spinal cord injury.

The invention will now be further described by way of the following examples.

EXAMPLES

Abbreviations

EDC=1-ethyl-3-(3-dimethylaminopropyl) carbodiimide) hydrochloride; DMAP=4-dimethylaminopyridine; DMF=dimethylformamide; DMSO=dimethylsulfoxide; EtOAc=Ethyl acetate; RT=room temperature; THF=tetrahydrofuran; DCM=dichloromethane; MeOH=methyl alcohol; EtOH=ethylic alcohol; LHMDS=Lithium bis(trimethylsilyl)amide; m-CPBA=meta-Chloroperoxybenzoic acid; LC-MS=Liquid Chromatography/Mass Spectrometry; HPLC=high pressure liquid chromatography; MPLC=medium pressure liquid chromatography; SFC=Supercritical Fluid Chromatography; HATU=(Dimethylamino)-N,N-dimethyl(3H-[1,2,3]triazolo[4,5-b]pyridin-3-yloxy)methaniminium hexafluorophosphate.

General Experimental Details
Analytical Methods
Liquid Chromatography-Mass Spectrometry
Method 1

LC-MS was performed on a Waters 2795 Alliance HT HPLC with Waters 2996 Diode Array Detector coupled to a Micromass ZQ, single quadrupole mass spectrometer using a Phenomenex Luna C18 (2) column (5 µm, 100×4.6 mm plus guard cartridge) with a linear gradient of 5-95% acetonitrile/water (with 0.1% formic acid in each mobile phase) within 3.5 minutes and held at 95% for 2.0 minutes.

Method 2

LC-MS was performed on a Waters 2795 Alliance HT HPLC with Waters 2996 Diode Array Detector coupled to a Micromass ZQ, single quadrupole mass spectrometer using a Waters Xterra MS C18 column (5 µm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.

NMR $^1$H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-Phase HPLC Conditions
Preparative HPL—Method 1
Waters Micromass ZQ/Sample manager 2767
Photodiode array detector 2996;
Column: XTerra Prep MS C18 Column (5 µm, 19×150 mm, Waters)
Flow rate: 20 ml/min with MS detection
UV wavelength: 254 nm.
Mobile phase: Solvent A (water:MeCN:HCOOH 95:5: 0.05); Solvent B (water:MeCN:HCOOH 5:95:0.05)
Gradient:

| Time (min) | % A | % B |
|---|---|---|
| 0.00 | 100.0 | 0.00 |
| 1.00 | 100 | 0.00 |
| 10.00 | 0.00 | 100.0 |
| 11.00 | 0.00 | 100.0 |
| 12.00 | 100.0 | 0.00 |

The above method, or slightly modifications known to the skilled in the art, were used.

Compound Preparation

Where the preparation of starting materials is not described, these are commercially available, known in the literature, or readily obtainable by those skilled in the art using standard procedures. Where it is stated that compounds were prepared "analogously" or "similarly" to earlier examples or intermediates, it will be appreciated by the skilled person that the reaction time, number of equivalents of reagents and temperature can be modified for each specific reaction and that it may be necessary or desirable to employ different work-up or purification techniques.

Flash chromatography refers to silica gel chromatography and is carried out using an Isolera MPLC system (manufactured by Biotage); pre-packed silica gel cartridges (supplied by Biotage); or using conventional glass column chromatography.

In the procedures that follow, after each starting material, reference to a compound number is made is typically provided. This is provided merely for assistance to the skilled chemist. The starting material may not necessarily have been prepared from the batch referred to.

Many of the Compounds described in the following Examples have been prepared from stereochemically pure starting materials, for example 95% ee.

The stereochemistry of the compounds in the Examples, where indicated, has been assigned on the assumption that absolute configuration at resolved stereogenic centers of staring materials in maintained throughout any subsequent reaction conditions.

Intermediate 1

[(1S)-2-(3,5-Dichloro-1-oxido-pyridin-1-ium-4-yl)-1-(3,4-dimethoxyphenyl)ethyl] 3-formyl-benzoate

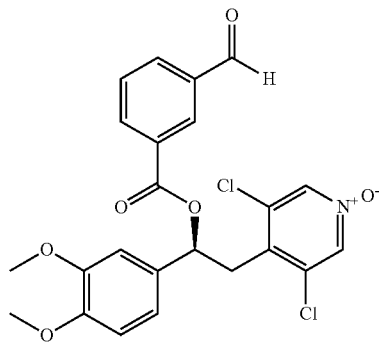

A solution of (S)-3,5-dichloro-4-(2-(3,4-dimethoxyphenyl)-2-hydroxyethyl)pyridine 1-oxide (described in the co-pending international application n. PCT/EP2013/075526 as Compound I 32/A) (0.688 g, 2 mmol), 3-formylbenzoic acid (0.300 g, 2 mmol), N-(3-dimethylaminopropyl)-N'-ethylcarbodiimide hydrochloride (0.767 g, 4 mmol) and 4-(dimethylamino)pyridine (0.122 g, 1 mmol) in anhydrous DCM (30 mL) was stirred at RT for 21 h. The reaction mixture was partitioned between saturated aqueous NaHCO$_3$ (20 mL) and DCM (10 mL) and filtered through a phase separator. The solvent was removed in vacuo and the crude material was purified by silica gel column chromatography eluting with 1:1 DCM:EtOAc to afford the title compound as an off-white solid (0.863 g, 91%).

$^1$H NMR (400 MHz, CDCl$_3$): δ 10.08 (s, 1 H), 8.54 (t, J=1.7 Hz, 1 H), 8.27 (dt, J=7.8, 1.5 Hz, 1 H), 8.14 (s, 2 H), 8.09 (dt, J=7.7, 1.5 Hz, 1 H), 7.63 (t, J=7.7 Hz, 1 H), 7.05 (dd, J=8.2, 2.1 Hz, 1 H), 7.00 (d, J=2.1 Hz, 1 H), 6.87 (d, J=8.3 Hz, 1 H), 6.33 (dd, J=9.7, 4.6 Hz, 1 H), 3.92 (s, 3 H), 3.88 (s, 3 H), 3.76 (dd, J=14.0, 9.8 Hz, 1 H), 3.39 (dd, J=14.0, 4.6 Hz, 1 H). LCMS (Method 1): [MH+]=476 at 3.55 min.

The following compounds were synthesised similarly to the method used for the Intermediate 1 starting from the suitable benzoic acids:

Intermediate 3

[(1S)-2-(3,5-dichloro-1-oxido-pyridin-1-ium-4-yl)-1-(3,4-dimethoxyphenyl)ethyl] 4-[[2-(dimethylaminomethyl)anilino]methyl]benzoate

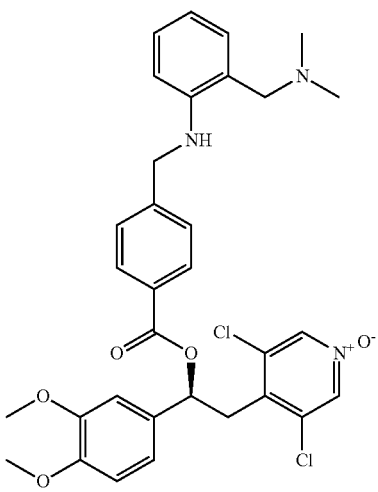

To a solution of [(1S)-2-(3,5-dichloro-1-oxido-pyridin-1-ium-4-yl)-1-(3,4-dimethoxyphenyl)ethyl] 4-formylbenzoate (Intermediate 2 herein described) (168 mg, 0.35 mmol) and 2-((dimethylamino)methyl)aniline (80.0 mg, 0.53 mmol) in anhydrous DCM (8.0 mL) was added acetic acid (0.040 mL, 0.53 mmol). The mixture was stirred at room temperature for 20 h. NaBH(OAc)$_3$ (186 mg, 0.88 mmol) was added and the mixture was stirred at room temperature for 24 h. The mixture was diluted with DCM (10 mL) and washed with saturated Na$_2$CO$_3$ solution (2×10 mL) and brine (10 mL), the organic phase was filtered through a phase separator and the solvent was removed in vacuo to afford the title compound as a colourless gum (211 mg, 98%).

LCMS (Method 1): [MH+]=610.

The following compounds were synthesised similarly to the method used for the Intermediate 3 starting from the suitable anilines:

| Structure | Intermediate number | Analytical Data |
|---|---|---|
| 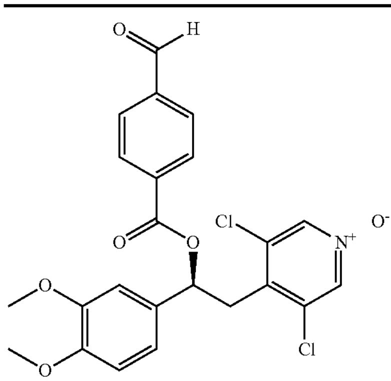 | Intermediate 2 | $^1$H NMR (400 MHz, CDCl$_3$): δ 10.10 (s, 1 H), 8.18 (d, J = 8.0 Hz, 2 H), 8.13 (s, 2 H), 7.95 (d, J = 8.0 Hz, 2 H), 7.05-6.99 (m, 2 H), 6.87 (d, J = 8.4 Hz, 1 H), 6.33 (dd, J = 4.4, 9.6 Hz, 1 H), 3.91 (s, 3 H), 3.88 (s, 3 H), 3.75 (dd, J = 9.6, 14.0 Hz, 1 H), 3.38 (dd, J = 4.4, 14.0 Hz, 1 H). LCMS (method 1): [MH+] = 476 at 3.65 min. |

| Structure | Intermediate number | Precursor | Analytical Data |
|---|---|---|---|
| 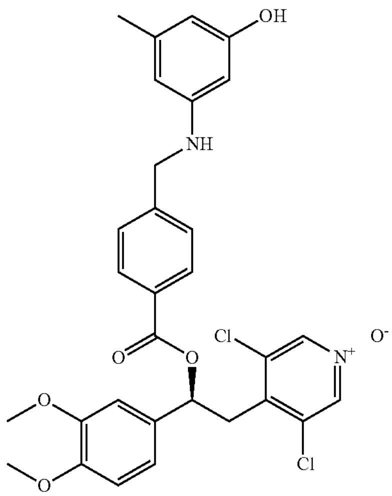 | Intermediate 4 | Intermediate 2 | LCMS (Method 1): [MH+] = 583. |
| 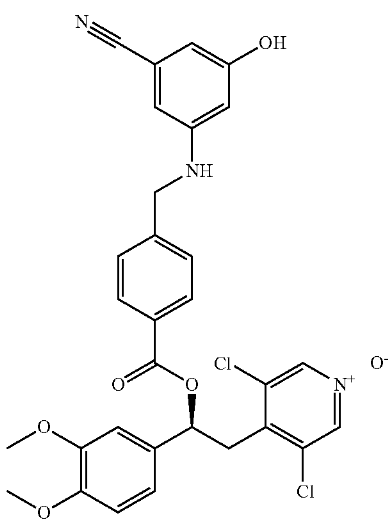 | Intermediate 5 | Intermediate 2 | LCMS (Method 1): [MH+] = 594. |
| 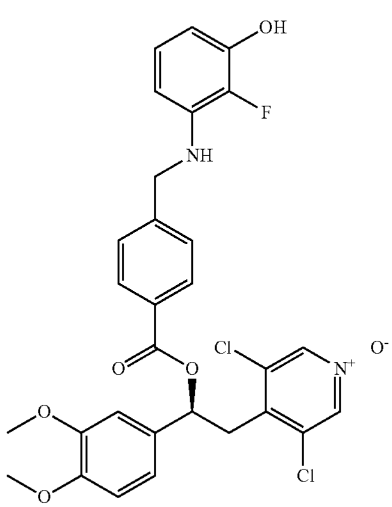 | Intermediate 6 | Intermediate 2 | LCMS (Method 1): [MH+] = 587. |

-continued

| Structure | Intermediate number | Precursor | Analytical Data |
|---|---|---|---|
| 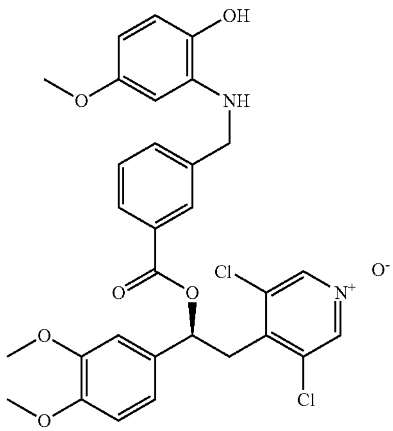 | Intermediate 7 | Intermediate 1 | LCMS (Method 2): [MH+] = 599. |
| 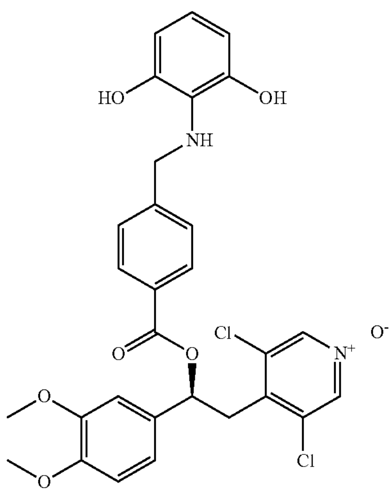 | Intermediate 8 | Intermediate 2 | LCMS (Method 2): [MH+] = 585 |
| 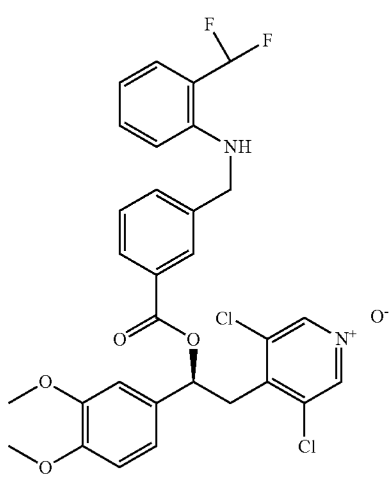 | Intermediate 9 | Intermediate 1 | LCMS (Method 2): [MH+] = 603 |

Intermediate 10 methyl 4-(3-anilinopropyl)benzoate

Step 2: Preparation of methyl 4-(3-oxopropyl)benzoate

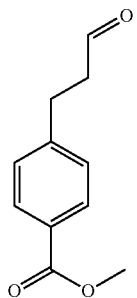

A solution of methyl-4-iodobenzoate (4.00 g, 5.27 mmol), sodium bicarbonate (3.21 g, 38.18 mmol), allyl alcohol (1.56 mL, 22.90 mmol), tetrabutyl ammonium bromide (4.92 g, 15.27 mmol) and 4 Å molecular sieves (3 g) in DMF (50 mL) was degassed with $N_2$ for 10 min. Palladium acetate (103 mg, 0.46 mmol) was then added and the resultant solution was stirred at room temperature under $N_2$ gas for 72 hours. The reaction mixture was filtered through a pad of Celite®, the filtrate was poured onto $H_2O$ (50 mL) and extracted with EtOAc (3×50 mL). The combined organic extracts were dried over $Na_2SO_4$ and concentrated in vacuo. The residue was purified by silica gel chromatography, eluting with 0-50% EtOAc in iso-hexane to give the title compound as a yellow oil (2.82 g, 96% yield).

$^1$H NMR (400 MHz, CDCl$_3$): δ 9.83 (t, J=1.2 Hz, 1 H), 7.97 (d, J=8.2 Hz, 2 H), 7.28 (s, 1H), 7.26 (s, 1 H), 3.91 (s, 3 H), 3.02 (t, J=7.3 Hz, 2 H), 2.82 (t, J=7.6 Hz, 2 H).

Step 2: Preparation of methyl 4-(3-anilinopropyl)benzoate

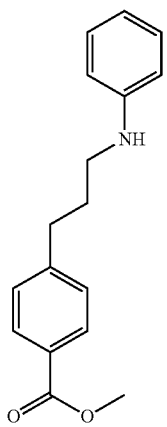

To a solution of methyl 4-(3-oxopropyl)benzoate (500 mg, 2.60 mmol) in ethanol (48 mL) was added aniline (474 μL, 5.20 mmol) and acetic acid (298 μL, 5.20 mmol) and the mixture was stirred at room temperature for 10 min. Sodium cyanoborohydride (327 mg, 5.20 mmol) was added and the reaction mixture was stirred at room temperature for 16 hours. The solvent was removed in vacuo and the residue partitioned between $H_2O$ (30 mL) and EtOAc (30 mL). The combined organic layers were dried ($Na_2SO_4$), filtered and concentrated in vacuo. The residue was purified by silica gel chromatography, eluting with 0-100% DCM in iso-hexane to give the title compound as a yellow oil (639 mg, 91% yield).

$^1$H NMR (400 MHz, CDCl$_3$): δ 7.96 (d, J=8.2 Hz, 2 H), 7.19-7.13 (m, 2 H), 6.78-6.68 (m, 3 H), 6.58 (d, J=7.6 Hz, 2 H), 3.91 (s, 3 H), 3.16 (t, J=7.0 Hz, 2 H), 2.79 (t, J=8.1 Hz, 2 H), 2.01-1.92 (m, 2 H). LCMS (Method 2): [MH+]=270

The following intermediate was synthesised via a similar method starting from methyl 2-fluoro-4-iodobenzoate:

| Structure | Intermediate number | Analytical Data |
|---|---|---|
| methyl 4-[3-(2-fluoroanilino)-propyl]benzoate 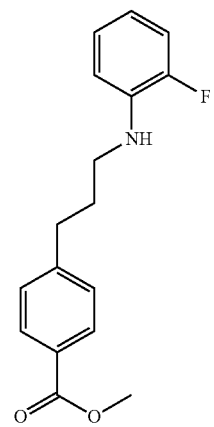 | Intermediate 11 | $^1$H NMR (400 MHz, CDCl$_3$): δ 7.97 (d, J = 8.2 Hz, 2 H), 7.01-6.91 (m, 2 H), 6.81-6.75 (m, 1 H), 6.72-6.58 (m, 3 H), 3.91 (s, 3 H), 3.18 (q, J = 6.5 Hz, 2 H), 2.80 (t, J = 7.9 Hz, 2 H), 2.04-1.96 (m, 2 H). LCMS (Method 2): [MH+] = 288 |

Intermediate 12 methyl 4-[3-(N-[(3R)-quinuclidin-3 yl]oxycarbonylanilino)propyl]benzoate

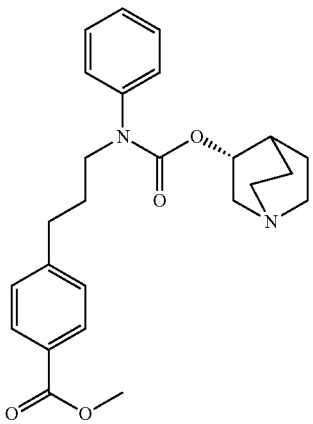 [SMILES: COC(=O)c1ccc(CCCN(C(=O)O[C@H]2CN3CCC2CC3)c2ccccc2)cc1]

A suspension of methyl 4-(3-anilinopropyl)benzoate (600 mg, 2.23 mmol) (Intermediate 10 herein described) and (R)-quinuclidin-3-yl carbonochloridate hydrochloride (described in the co-pending international application n. PCT/EP2013/075526 as compound I-1) (1.00 g, 4.46 mmol) in anhydrous CH₃CN (5 mL) was heated in the microwave at 100° C. for 20 min. After cooling to room temperature, the solvent was removed in vacuo and the residue partitioned was between EtOAc (30 mL) and saturated aqueous NaHCO₃ (30 mL). The layers were separated and the organic phase was dried over MgSO₄, filtered and the solvent removed in vacuo. Purification by silica gel chromatography sequentially eluting with ethyl acetate and 10% 7 N methanolic ammonia in ethyl acetate gave the title compound as a yellow oil (639 mg, 91% yield).

$^1$H NMR (400 MHz, CDCl₃): δ 7.92 (d, J=9.1 Hz, 2 H), 7.39-7.30 (m, 5 H), 7.18 (d, J=8.7 Hz, 2 H), 4.86-4.81 (m, 1 H), 3.90 (s, 3 H), 3.73 (dt, J=1.5, 7.1 Hz, 2 H), 3.33-3.25 (m, 1 H), 2.94-2.63 (m, 6 H), 1.95-1.84 (m, 2 H), 1.75-1.39 (m, 6 H). LCMS (Method 2): [MH+]=423.

The following intermediate was synthesised via a similar method starting from Intermediate 11 above described:

| Structure | Intermediate number | Analytical Data |
|---|---|---|
| methyl 4-[3-(2-fluoro-N-[(3R)-quinuclidin-3-yl]oxycarbonyl-anilino)propyl]-benzoate | Intermediate 13 | $^1$H NMR (400 MHz, CDCl₃): δ 7.92 (d, J = 8.0 Hz, 2 H), 7.21-6.98 (m, 6 H), 4.86-4.82 (m, 1 H), 3.90 (s, 3 H), 3.74-3.64 (m, 2 H), 3.33-3.25 (m, 1 H), 2.96-2.59 (m, 6 H), 1.91-1.85 (m, 4 H), 1.77-1.68 (m, 1 H), 1.52-1.39 (m, 2 H), 1.21-1.14 (m, 1 H). LCMS (Method 1): [MH+] = 441 |

Intermediate 1A (R)-Quinuclidin-3-yl carbonochloridate hydrochloride

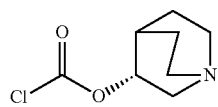 [SMILES: O=C(Cl)O[C@H]1CN2CCC1CC2]

To a stirred solution of (R)-3-quinuclidinol (2.5 g, 19.66 mmol) in acetonitrile (200 mL) was added trichloromethyl chloroformate (3.06 mL, 25.57 mmol) dropwise at 0° C. and the mixture was allowed to stir at 0° C. for 1 hour. The reaction mixture was then stirred at RT for 16 hours and then the solvent was removed in vacuo to afford the title compound as a white solid (4.39 g, 98%).

$^1$H NMR (400 MHz, DMSO-d₆): δ 10.29 (s, 1 H), 4.05-3.95 (m, 1 H), 3.43 (t, J=10.8 Hz, 1 H), 3.12 (m, 3 H), 3.10-2.95 (m, 1 H), 2.79 (d, J=13.3 Hz, 1 H), 2.12-2.02 (m, 1 H), 1.98 (m, J=3.4 Hz, 1 H), 1.89-1.78 (m, 1 H), 1.75-1.59 (m, 2 H).

Intermediate 2A (S)-3,5-Dichloro-4-(2-(3,4-dimethoxyphenyl)-2-hydroxyethyl)pyridine 1-oxide

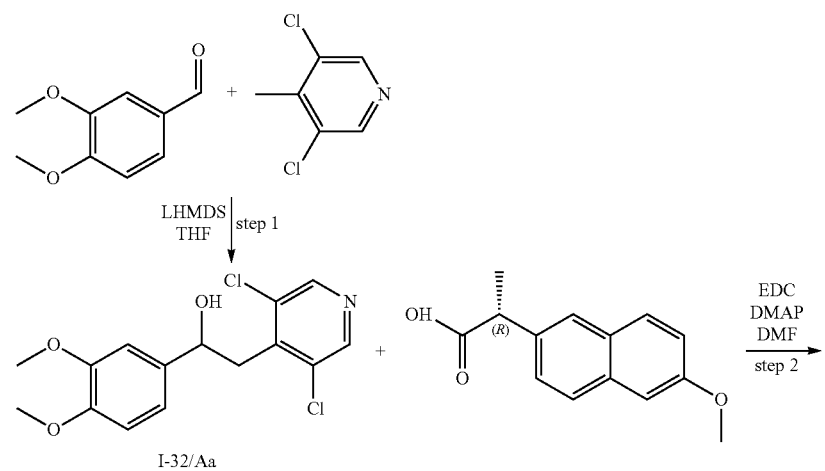

I-32/Aa

-continued

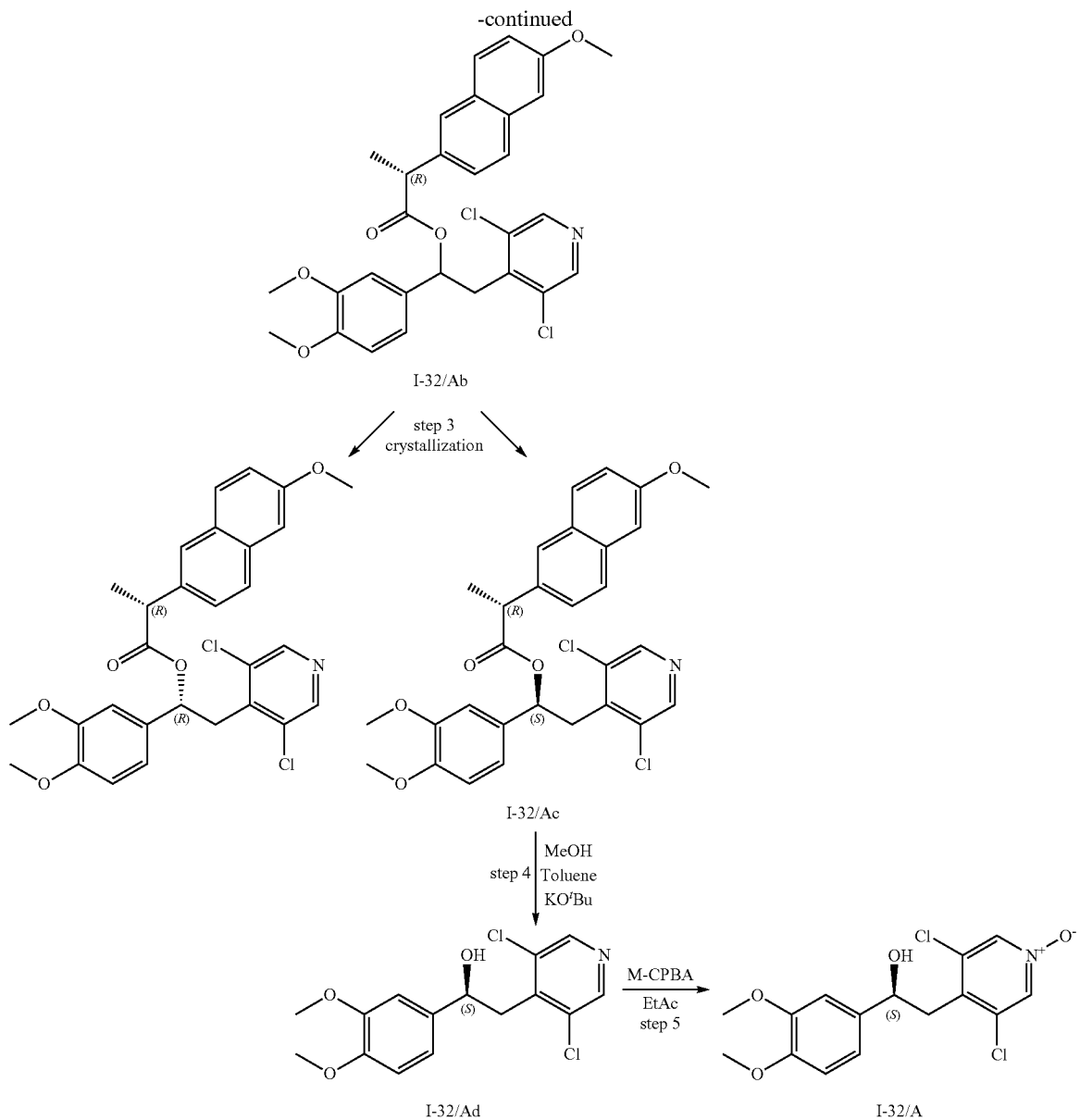

Step 1: Preparation of (R,S)-2-(3,5-dichloropyridin-4-yl)-1-(3,4-dimethoxyphenyl)ethanol (I-32/Aa)

3,5-Dichloro-4-methylpyridine (54 g, 331 mmol) was dissolved in dry THF (480 mL) under Argon atmosphere and cooled at −78° C. in dry-ice/acetone bath. LHMDS 1N THF solution (331 mL, 331 mmol) was added drop-wise keeping the temperature at −78°. The mixture was stirred at −78° for 1 h. Thereafter, a solution of 3,4-dimethoxybenzaldehyde (50 g, 301 mmol) in dry THF (120 mL) was added drop-wise keeping the temperature at −78° C. When the addition was completed, the mixture was allowed to warm at RT.

The reaction was poured into ice and water (1 L) and the mixture was stirred until a copious precipitate formed. The solid was filtered, and dissolved in Ethyl Acetate (500 mL), dried over $Na_2SO_4$ and the solvent evaporated under vacuum. The crude was crystallized in $CHCl_3$/Hexane. The precipitate was filtered, washed with hexane and dried under vacuum at 40° C. for 8 h to give 55 g of the title compound (45% yield). The mother liquor solution was evaporated under vacuum at 40° C., dissolved in ethyl acetate (200 mL) and extracted with 200 mL of water. The organic solution was dried over $Na_2SO_4$ and the solvent evaporated under vacuum at 40° C. The crude was crystallized in $CHCl_3$/Hexane, and additional 15 g of the title product were obtained (70% overall yield).

Step 2: Preparation of (R,S)-2-(3,5-dichloropyridin-4-yl)-1-(3,4-dimethoxyphenyl)ethyl (R)-2-(6-methoxynaphthalen-2-yl)propanoate (I-32/Ab)

(R,S)-2-(3,5-dichloropyridin-4-yl)-1-(3,4-dimethoxyphenyl)ethanol (50 g, 152 mmol), (R)-2-(6-methoxynaphthalen-2-yl)propanoic acid (38.6 g, 168 mmol), DMAP (20.5 g, 168 mmol) and EDC (43.8 g, 229 mmol) were dissolved in DMF (300 mL) and the reaction mixture was stirred at RT for 2 h. Thereafter, water (500 mL) was added, and the solution stirred till complete precipitation occurs. The solid was filtered and dissolved in DCM (500 mL). The organic solution was washed with aqueous HCl 1N (2×500 mL), saturated aqueous NaHCO₃ solution (500 mL) and dried over Na₂SO₄. The solvent was evaporated under vacuum and the solid residue sonicated in EtOH (300 mL) and triturated for 1 h. The resulting precipitate was collected by filtration and dried under vacuum at 40° C. for 4 h to give 79 g (99% yield) of the title compound, as diastereoisomeric mixture.

Step 3: Preparation of (S)-2-(3,5-dichloropyridin-4-yl)-1-(3,4-dimethoxyphenyl)ethyl) (R)-(2-(6-methoxynaphthalen-2-yl)propanoate (I-32/Ac)

(R,S)-2-(3,5-dichloropyridin-4-yl)-1-(3,4-dimethoxyphenyl)ethyl) (R)-(6-methoxynaphthalen-2-yl)propanoate (diastereoisomeric mixture, 79 g, 146 mmol) was dissolved in CHCl₃ (100 mL) and MeOH (30 mL) was slowly added up to persistent opalescence and the mixture left at RT for 2 h. The solid formed was collected by filtration and re-crystallized by CHCl₃/MeOH (70 mL/20 mL) solvent system to obtain 35 g of the desired compound (yield 88%, ee 98%). Chiral HPLC analysis: Chiralcel OD column, 10 µm, 250×4.6 mm; Flow=0.8 ml/min; eluent=hexane:isopropanol 97/3; Rt=42.33 min; $^1$H NMR (600 MHz, chloroform-d) δ ppm 8.04 (s, 2 H), 7.67 (d, J=8.79 Hz, 1 H), 7.58 (d, J=8.52 Hz, 1 H), 7.53 (m, 1 H), 7.12-7.20 (m, 3 H), 6.95 (dd, J=8.24, 1.92 Hz, 1 H), 6.78-6.88 (m, 2 H), 6.14 (dd, J=10.44, 4.12 Hz, 1 H), 3.95 (s, 3 H), 3.88 (s, 3 H), 3.78-3.81 (m, 4 H), 3.55 (dd, J=13.73, 10.44 Hz, 1 H), 3.14 (dd, J=13.60, 4.26 Hz, 1 H), 1.44 (d, J=7.14 Hz, 3 H).

Step 4: Preparation of (S)-2-(3,5-dichloropyridin-4-yl)-1-(3,4-dimethoxyphenyl)ethanol, (I-32/Ad)

(S)-2-(3,5-dichloropyridin-4-yl)-1-(3,4-dimethoxyphenyl)ethyl) (R)-2-(6-methoxynaphthalen-2-yl)propanoate (30 g, 56 mmol) was dissolved in MeOH, and toluene was slowly added. Potassium tert-butoxide was slowly added to the suspension. The mixture was stirred for 24 h at RT. The reaction was diluted with water (500 mL) and the aqueous mixture was extracted with CHCl₃ (500 mL). The organic layer was dried over Na₂SO₄ and the solvent was evaporated under vacuum. The residue was crystallized from CHCl₃ (100 mL) and Hexane (20 mL). The mother liquor was concentrated and recrystallized with an analogous procedure giving a second crop of desired compound. In total, 16 g of the title compound (87% yield) were obtained. Chiral HPLC analysis; Chiralcel OD column, 10 µm, 250×4.6 mm; flow=0.8 ml/min; eluent=hexane:isopropanol 95/5; Rt=58.03 min; [α]$_D^{20}$=+10.21 (c=0.506, Methanol); $^1$H NMR (400 MHz, acetone) 6 ppm 8.47 (s, 2 H), 6.96-7.15 (m, 1 H), 6.87 (m, 2 H), 4.93-5.21 (m, 1 H), 4.50 (d, J=3.97 Hz, 1 H), 3.78 (s, 6 H), 3.44 (dd, J=12.79, 8.38 Hz, 1 H), 3.22 (dd, J=13.01, 5.51 Hz, 1 H). MS/ESI⁺ [MH]⁺: 328.19

Step 5: Preparation of (S)-3,5-dichloro-4-(2-(3,4-dimethoxyphenyl)-2-hydroxyethyl)pyridine 1-oxide (I-32/A)

(S)-2-(3,5-Dichloropyridin-4-yl)-1-(3,4-dimethoxyphenyl)ethanol (4 g, 12 mmol) was dissolved in Ethyl Acetate, and m-CPBA was added to the solution. The mixture was stirred at RT for 5 h. The formed solid was collected by filtration, washed with ethyl acetate and dried under vacuum to give 1.72 g of (S)-2-(3,5-dichloropyridin-4-yl)-1-(3,4-dimethoxyphenyl)ethanol (41% yield). Chiral HPLC analysis: Chiralcel OD column, 10 µm, 250×4.6 mm; Flow=0.8 ml/min; eluent=hexane:isopropanol 60/40; Rt=22.16 min; [α]$_D^{20}$=+68.91 (c=0.253, Methanol/CHCl3 1:1); 1H NMR (400 MHz, chloroform-d) δ ppm 8.15 (s, 2 H), 6.99 (m, 1 H), 6.79-6.88 (m, 2 H), 5.03 (dd, J=8.50, 5.32 Hz, 1 H), 3.75-3.98 (m, 6 H), 3.42 (dd, J=13.57, 8.56 Hz, 1 H), 3.19 (dd, J=13.51, 5.32 Hz, 1 H), 2.06-2.15 (m, 1 H); MS/ESI⁺ [MH]⁺: 344

Example 1

[(1S)-2-(3,5-dichloro-1-oxido-pyridin-1-ium-4-yl)-1-(3,4-dimethoxyphenyl)ethyl] 4-[[2-(dimethylaminomethyl)-N-[(3R)-quinuclidin-3-yl]oxycarbonyl-anilino]methyl]benzoate

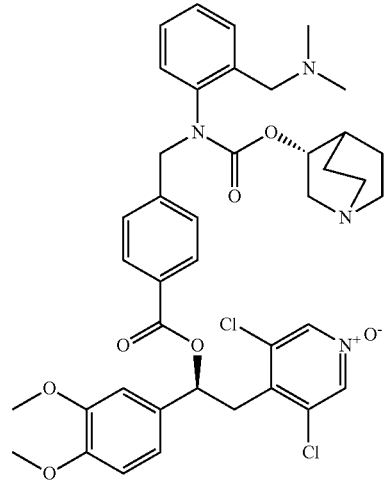

A mixture of [(1S)-2-(3,5-dichloro-1-oxido-pyridin-1-ium-4-yl)-1-(3,4-dimethoxyphenyl)ethyl] 4-[[2-(dimethylaminomethyl)anilino]methyl]benzoate (Intermediate 3 herein described) (69 mg, 0.11 mmol) and [(3R)-quinuclidin-3-yl] carbonochloridate (described in the international application n. PCT/EP2013/075526 as compound I-1) (51 mg, 0.22 mmol) in CH₃CN (3 mL) was heated in the microwave at 80° C. for 6 min. The mixture was partitioned between EtOAc (2×10 mL) and water (5 mL), the combined organic extracts were back extracted with water (5 mL). The combined aqueous phase was basified with saturated NaHCO₃ solution and extracted with EtOAc (2×10 mL). The organic phases were combined, filtered through a phase separator and concentrated in vacuo. Purification by preparative HPLC gave the title compound as a light brown solid, (14.5 mg, 17%).

$^1$H NMR (400 MHz, DMSO): δ 8.54 (s, 2 H), 7.93 (d, J=7.6 Hz, 2 H), 7.48-7.45 (m, 3 H), 7.30-7.15 (m, 3 H), 7.05-6.95 (m, 4 H), 6.21 (dd, J=4.3, 9.3 Hz, 1 H), 5.06-5.01 (m, 1 H), 4.63-4.54 (m, 2 H), 3.77 (d, J=10.9 Hz, 7 H), 3.66-3.59 (m, 1 H), 3.25-3.10 (m, 2 H), 3.08-3.05 (m, 1 H), 2.68 (dd, J=1.9, 1.9 Hz, 1 H), 2.36-2.31 (m, 3 H), 2.05 (dd, J=8.5, 8.5 Hz, 6 H), 1.73-1.30 (m, 5 H).

LCMS (Method 1): [MH+]=763 at 2.30 min.

The following compounds were synthesised similarly to the method used for Example 1 starting from Intermediates 4-9 above described:

| Structure | Example number | Analytical Data |
|---|---|---|
| [(1S)-2-(3,5-dichloro-1-oxido-pyridin-1-ium-4-yl)-1-(3,4-dimethoxyphenyl)ethyl] 4-[(3-hydroxy-5-methyl-N-[(3R)-quinuclidin-3-yl]oxycarbonyl-anilino)methyl]benzoate 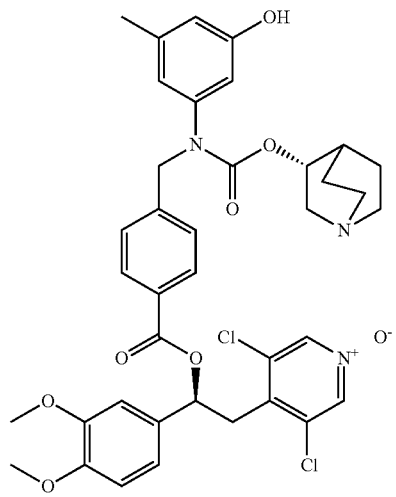 | Example 2 | $^1$H NMR (400 MHz, DMSO) δ 9.38 (s, 1 H), 8.54 (s, 2 H), 7.97 (d, J = 8.1 Hz, 2 H), 7.39 (d, J = 8.1 Hz, 2 H), 7.06-6.99 (m, 2 H), 6.96 (d, J = 8.3 Hz, 1 H), 6.56 (s, 1 H), 6.46 (s, 1 H), 6.42 (s, 1 H), 6.21 (dd, J = 4.3, 9.6 Hz, 1 H), 4.89 (d, J = 5.3 Hz, 2 H), 4.66-4.60 (m, 1 H), 3.78 (s, 3 H), 3.75 (s, 3 H), 3.62 (dd, J = 9.7, 14.0 Hz, 1 H), 3.33-3.27 (m, 1 H), 3.04 (dd, J = 7.8, 13.9 Hz, 1 H), 2.65-2.53 (m, 3 H), 2.44 (d, J = 15.2 Hz, 2H), 2.16 (s, 3 H), 1.85-1.80 (m, 1 H), 1.59-1.42 (m, 2 H), 1.32-1.13 (m, 2 H).<br>LCMS (Method 2): [MH+] = 736 |
| [(1S)-2-(3,5-dichloro-1-oxido-pyridin-1-ium-4-yl)-1-(3,4-dimethoxyphenyl)ethyl] 4-[(3-cyano-5-hydroxy-N-[(3R)-quinuclidin-3-yl]oxycarbonyl-anilino)methyl]benzoate 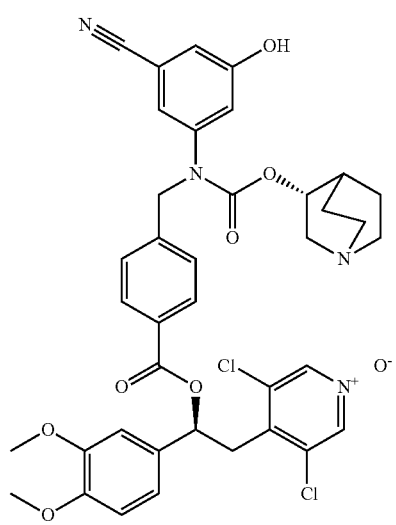 | Example 3 | $^1$H NMR (400 MHz, DMSO) δ 10.45 (brs, 1 H), 8.63 (s, 2 H), 8.05 (d, J = 8.1 Hz, 2 H), 7.49 (d, J = 8.3 Hz, 2 H), 7.40 (s, 1 H), 7.15-7.08 (m, 3 H), 7.05 (d, J = 8.1 Hz, 2 H), 6.30 (dd, J = 4.3, 9.6 Hz, 1 H), 5.07 (s, 2 H), 4.77-4.75 (m, 1 H), 3.86 (s, 3 H), 3.84 (s, 3 H), 3.71 (dd, J = 9.7, 14.0 Hz, 1 H), 3.45-3.32 (m, 1 H), 3.19-3.11 (m, 1 H), 2.73-2.63 (m, 3 H), 2.48-2.39 (m, 1 H), 1.97-1.91 (m, 1 H), 1.69-1.60 (m, 1 H), 1.57-1.51 (m, 1 H), 1.38-1.25 (m, 3H).<br>LCMS (Method 1): [MH+] = 747 |

| Structure | Example number | Analytical Data |
|---|---|---|
| [(1S)-2-(3,5-dichloro-1-oxido-pyridin-1-ium-4-yl)-1-(3,4-dimethoxyphenyl)ethyl] 4-[(2-fluoro-3-hydroxy-N-[(3R)-quinuclidin-3-yl]oxycarbonyl-anilino)methyl]benzoate 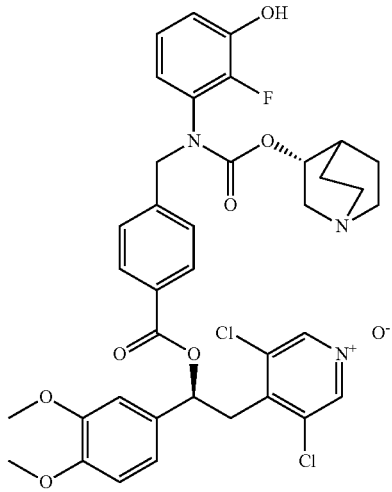 | Example 4 | $^1$H NMR (400 MHz, DMSO) δ 10.05-9.99 (m, 1 H), 8.55 (s, 2 H), 7.94 (d, J = 7.3 Hz, 2 H), 7.41-7.36 (m, 2 H), 7.06-6.98 (m, 2 H), 6.96 (d, J = 8.3 Hz, 1 H), 6.92-6.89 (m, 1 H), 6.88-6.83 (m, 1 H), 6.74-6.70 (m, 1 H), 6.20 (dd, J = 4.3, 9.1 Hz, 1 H), 4.86-4.85 (m, 2 H), 4.67-4.62 (m, 1 H), 3.77 (s, 3 H), 3.75 (s, 3 H), 3.62 (dd, J = 9.6, 14.1 Hz, 1 H), 3.37-3.28 (m, 1 H), 3.12-3.03 (m, 1 H), 2.63-2.54 (m, 4 H), 2.48-2.42 (m, 1 H), 1.81-1.79 (m, 1 H), 1.55-1.53 (m, 1 H), 1.48-1.41 (m, 1 H), 1.24-1.12 (m, 2 H). LCMS (Method 1): [MH+] = 740 |
| [(1S)-2-(3,5-dichloro-1-oxido-pyridin-1-ium-4-yl)-1-(3,4-dimethoxyphenyl)ethyl] 3-[(2-hydroxy-5-methoxy-N-[(3R)-quinuclidin-3-yl]oxycarbonyl-anilino)methyl]benzoate 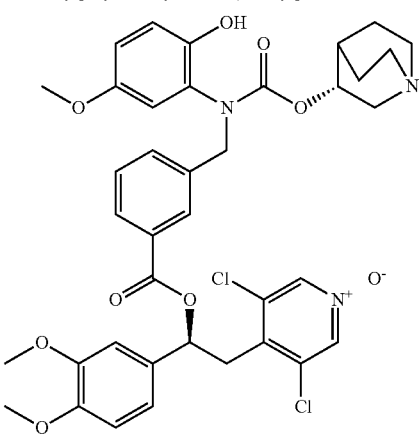 | Example 5 | 1H NMR (400 MHz, DMSO) δ 9.54-9.05 (bs, 1 H), 8.51 (s, 2 H), 8.18 (s, 1 H), 8.05-7.80 (m, 2 H), 7.68-7.32 (m, 2 H), 7.10-6.86 (m, 3 H), 6.84-6.66 (m, 2 H), 6.47 (m, 1 H), 6.20 (m, 1 H), 4.84-4.46 (m, 3 H), 3.88 (s, 3 H), 3.68 (s, 3 H), 3.54-3.32 (m, 4 H), 3.34-3.12 (m, 2 H), 2.63-2.40 (m, 5 H), 1.83 (m, 1 H), 1.55-1.40 (m, 4 H). LCMS (Method 2): [MH+] = 752 |

-continued

| Structure | Example number | Analytical Data |
|---|---|---|
| [(1S)-2-(3,5-dichloro-1-oxido-pyridin-1-ium-4-yl)-1-(3,4-dimethoxyphenyl)ethyl] 4-[(2,6-dihydroxy-N-[(3R)-quinuclidin-3-yl]oxycarbonyl-anilino)methyl]benzoate formate salt 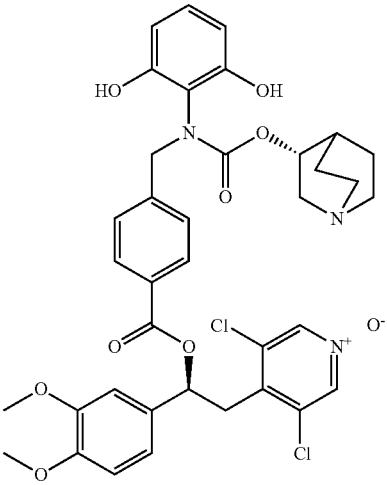 | Example 6 | 1H NMR (400 MHz, DMSO) δ 9.51-9.33 (m, 2 H), 8.54 (s, 2 H), 8.18 (s, 1 H), 7.84 (m, 2 H), 7.56-7.42 (m, 2 H), 7.07-6.90 (m, 4 H), 6.84-6.74 (m, 1 H), 6.26 (d, J = 8.4 Hz, 2 H), 6.21-6.14 (m, 1 H), 4.82-4.51 (m, 3 H), 3.70 (s, 3 H), 3.81 (s, 3 H), 3.67-3.53 (m, 1 H), 3.11-2.93 (m, 1 H), 2.71-2.53 (m, 6 H), 1.79-1.69 (m, 1 H), 1.60-1.38 (m, 4 H).<br>LCMS (Method 2): [MH+] = 738 |
| [(1S)-2-(3,5-dichloro-1-oxido-pyridin-1-ium-4-yl)-1-(3,4-dimethoxyphenyl)ethyl] 3-[[2-(difluoromethyl)-N-[(3R)-quinuclidin-3-yl]oxycarbonyl-anilino]methyl]benzoate 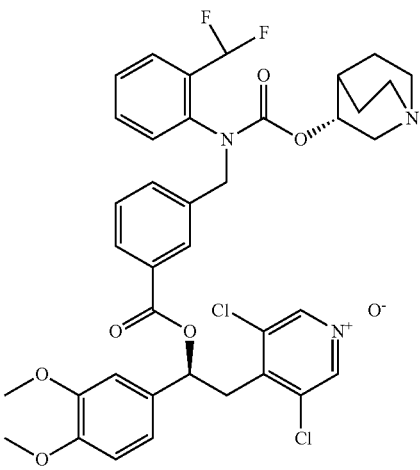 | Example 7 | $^1$H NMR (400 MHz, DMSO, 125° C.): δ 8.28 (s, 2 H), 7.88-7.85 (m, 2 H), 7.63-7.59 (m, 1 H), 7.51-7.41 (m, 4 H), 7.10-6.94 (m, 4 H), 6.75 (t, J = 54.6 Hz, 1 H), 6.26 (dd, J = 4.9, 8.9 Hz, 1 H), 4.83 (br s, 2 H), 4.72-4.65 (m, 1 H), 3.78 (s, 3 H), 3.78 (s, 3 H), 3.61 (dd, J = 9.1, 14.2 Hz, 1 H), 3.38 (dd, J = 4.8, 14.1 Hz, 1 H), 3.10-3.02 (m, 1 H), 2.90-2.29 (m, 5 H), 1.83-1.78 (m, 1 H), 1.60-1.07 (m, 4 H).<br>LCMS (Method 1): [MH+] = 756 |

Example 8

[(1S)-2-(3,5-dichloro-1-oxido-pyridin-1-ium-4-yl)-1-(3,4-dimethoxyphenyl)-ethyl] 4-[3-(N-oxycarbonylanilino)propyl]benzoate

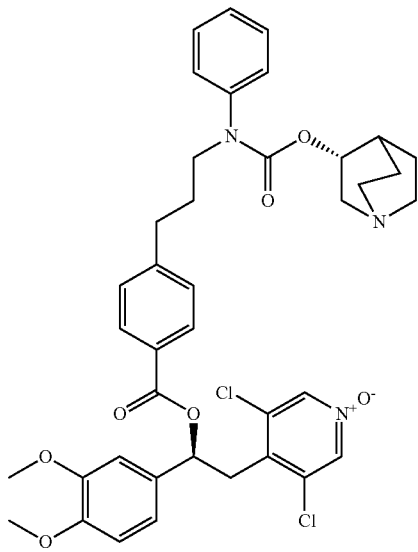

A solution of methyl 4-[3-(N-[(3R)-quinuclidin-3-yl]oxycarbonylanilino)propyl]benzoate (Intermediate 12) (439 mg, 1.04 mmol) in THF (4 mL) and MeOH (4 mL) was added with 1 N aqueous solution of LiOH (2.08 mL, 2.08 mmol). The resultant solution was stirred at room temperature for 16 hours. The reaction mixture was cooled to 0° C. and acidified to pH 1 with 2 N HCl. The solvent was removed in vacuo and the residue was azeotroped with toluene to yield a white solid that was redissolved in DMF (5 mL). (1S)-2-(3,5-dichloro-1-oxido-pyridin-1-ium-4-yl)-1-(3,4-dimethoxyphenyl)ethanol (described in the co-pending international application n. PCT/EP2013/075526 as Compound I 32/A) (429 mg, 1.25 mmol) followed by 4-(dimethylamino)-pyridine (63 mg, 0.52 mmol) and N-(3-dimethylaminopropyl)-N'-ethylcarbodiimide hydrochloride (399 mg, 2.08 mmol) were added and the mixture was stirred at room temperature for 18 hours. The reaction mixture was partitioned between EtOAc (15 mL) and saturated aqueous NaHCO$_3$ solution (15 mL). The organic layer was washed with brine (3×30 mL), dried (MgSO$_4$), filtered and the solvent was removed in vacuo. The residue was purified by preparative HPLC to provide title compound (140 mg) as an off-white solid.

$^1$H NMR (400 MHz, DMSO): δ 8.56 (s, 2 H), 7.87 (d, J=8.3 Hz, 2 H), 7.39 (t, J=7.7 Hz, 2 H), 7.32-7.23 (m, 5 H), 7.06-6.95 (m, 3 H), 6.20 (dd, J=4.3, 9.6 Hz, 1 H), 4.60-4.54 (m, 1 H), 3.78 (s, 3 H), 3.74 (s, 3 H), 3.70-3.58 (m, 3 H), 3.30 (d, J=4.3 Hz, 1 H), 3.05-2.98 (m, 1 H), 2.64 (t, J=7.6 Hz, 2 H), 2.60-2.52 (m, 3 H), 2.47-2.38 (m, 2 H), 1.81-1.73 (m, 3 H), 1.55-1.46 (m, 1 H), 1.45-1.37 (m, 1 H), 1.32-1.21 (m, 1 H), 1.18-1.08 (m, 1 H).

LCMS (Method 1): [MH+]=734

The following compound was synthesised similarly to the method of the example 8, starting from Intermediate 13:

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[3-(2-fluoro-N-[(3R)-quinuclidin-3-yl]oxycarbonyl-anilino)propyl]benzoate | Example 9 | Intermediate 11 | $^1$H NMR (400 MHz, DMSO): δ 8.54 (s, 2 H), 7.87 (d, J = 8.1 Hz, 2 H), 7.45-7.40 (m, 1 H), 7.38-7.33 (m, 1 H), 7.30 (d, J = 8.1 Hz, 3 H), 7.25-7.21 (m, 1 H), 7.04-6.94 (m, 3 H), 6.19 (dd, J = 4.4, 9.5 Hz, 1 H), 4.64-4.59 (m, 1 H), 3.77 (s, 3 H), 3.74 (s, 3 H), 3.66-3.53 (m, 3 H), 3.09 (dd, J = 7.6, 13.1 Hz, 1 H), 2.68-2.58 (m, 6 H), 2.47-2.40 (m, 2 H), 1.80-1.70 (m, 3 H), 1.58-1.50 (m, 1 H), 1.50-1.42 (m, 1 H), 1.21-1.12 (m, 2 H). LCMS (Method 1): [MH+] = 752 |

Pharmacological Activity of the Compounds of the Invention

In Vitro Determination of PDE4 Inhibitory Activity

In vitro determination of PDE4 inhibitory activity for compounds of the invention may be determined according to one of the protocols herebelow reported:

PDE4B2 HTRF Assay:

PDE4B2 activity is detected using the LANCE Ultra cAMP homogeneous time resolved fluorescence resonance energy transfer (TR-FRET) assay from Perkin Elmer. The assay is based on the competition between the europium (Eu) chelate-labeled cAMP tracer and sample cAMP for binding sites on cAMP-specific monoclonal antibodies (mAb) labelled with the ULight™ dye. The assay is carried out in 384-well low volume plates in a volume of 10 μl. Human recombinant PDE4B2 (80 pM) is incubated for 2 h with 3 nM cAMP in buffer containing 1×HBSS, 5 mM HEPES, 3 mM $MgCl_2$, 0.1% BSA, pH 7.4 with or without test compounds. The enzymatic reactions are efficiently stopped by the addition of 500 μM IBMX present in the combined Stop/Detection buffer containing europium (Eu) chelate-labeled cAMP tracer and cAMP-specific monoclonal antibodies (mAb) labelled with the ULight™ dye. Samples are then further incubated for 1 h before plates are read at ex 340 nm and em at 665 nm and 615 nm on an EnVision reader. $IC_{50}$ values are determined from competition curves using a non-linear curve fitting program.

PDE4 Cell Free Assay Protocol

PDE4 activity is determined in U937 human monocytic supernatants cells lysate. Cells are cultured, harvested and supernatant fraction prepared essentially as described in Torphy T J et al J. Pharmacol. Exp. Ther. 1992; 263:1195-1205.

U937 cells are grown at 37° C., 5% $CO_2$ in RPMI 1640 with GlutaMAX™-I medium supplemented with 10% fetal bovine serum and 100 μg/mL Pen-strep (Gibco).

Cells are harvested and washed twice by centrifugation (150×g, 8 min) in cold PBS. Washed cells are re-suspended in cold Krebs-Ringer-Henseleit buffer at a final concentration 20×10⁶ cells/mL and sonicated. After centrifugation at 15000×g for 20 min, the supernatants are pooled, divided in aliquots and stored at −80° C.

PDE4 activity is determined in cells supernatants by assaying cAMP disappearance from the incubation mixtures.

The concentration of the test compounds ranges between $10^{-12}$ M and $10^{-6}$ M. Reactions are stopped by enzyme heat inactivation (2.5 minutes at 100° C.) and residual cAMP content is determined using the 'LANCE cAMP Assay' from PerkinElmer following the provider instructions.

The results, expressed as mean±standard deviation of the molar concentration of the test compound producing 50% inhibition of cAMP disappearance ($IC_{50}$).

Percentage of inhibition of PDE4 activity is calculated, assuming cAMP disappearance in the absence of inhibitors as 100% and cAMP disappearance in heat inactivated samples as 0%.

Representative compounds of the invention, when tested in one of the above reported protocols, displayed an $IC_{50}$ lower than 100 nM.

In Vitro Determination of M3 Antagonism

In vitro determination of M3 antagonism for compounds of the invention may be determined according to one of the protocols herebelow reported:

M3 Receptor Radioligand Binding Assay:

Human $M_3$ receptor membranes (15 μg/well) from Perkin Elmer are incubated with 0.52 nM Scopolamine Methyl Chloride, [N-methyl-3H] with or without test compounds, or a saturating concentration of Atropine (5 μM) for the determination of non-specific binding. The assay is carried out in 96-well polypropylene plates in a volume of 250 μl. The assay buffer used is 50 mM Tris-HCl, 154 mM NaCl (pH 7.4). The final assay concentration of DMSO is 0.5% (v/v). The plates are sealed and incubated for 2 h at room temperature on an orbital shaker (slow speed). Membranes are harvested onto 96-well unifilter GF/C filter plates pre-treated with 0.5% polyethyleneimine (v/v), using a filter manifold, washed four times with 200 μl of assay buffer. The plates are dried before addition of 50 μl of microscint-0, sealed then read in a Trilux Microbeta scintillation counter. $IC_{50}$ values are determined from competition curves using a non-linear curve fitting program. $K_i$ values are calculated from $IC_{50}$ values by the Cheng and Prusoff equation.

M3 Binding Assay:

CHO—K1 clone cells expressing the human M3-receptor (Swissprot P20309) were harvested in $Ca^{++}/Mg^{++}$ free phosphate-buffered saline and collected by centrifugation at 1500 rpm for 3 min. The pellets were resuspended in ice cold buffer A (15 mM Tris-HCl pH 7.4, 2 mM $MgCl_2$, 0.3 mM EDTA, 1 mM EGTA) and homogenized by a PBI politron (setting 5 for 15 s). The crude membrane fraction was collected by two consecutive centrifugation steps at 40000 g for 20 min at 4° C., separated by a washing step in buffer A. The pellets obtained were finally resuspended in buffer B (75 mM Tris HCl pH 7.4, 12.5 mM $MgCl_2$, 0.3 mM EDTA, 1 mM EGTA, 250 mM sucrose), and aliquots were stored at −80° C.

The day of experiment, frozen membranes were resuspended in buffer C (50 mM Tris-HCl pH 7.4, 2.5 mM $MgCl_2$, 1 mM EDTA). The non selective muscarinic radioligand [$^3$H]—N-methyl scopolamine (*Mol. Pharmacol.* 45:899-907) was used to label the M3 binding sites. Binding experiments were performed in duplicate (ten point concentrations curves) in 96 well plates at radioligand concentration of 0.1-0.3 nM. The non specific binding was determined in the presence of cold N-methyl scopolamine 10 μM. Samples (final volume 0.75 mL) were incubated at room temperature for 90 min. The reaction was terminated by rapid filtration through GF/B Unifilter plates and two washes (0.75 mL) with cold buffer C using a Packard Filtermate Harvester. Radioactivity on the filters was measured by a microplate scintillation counter TriCarb 2500 (PerkinElmer).

Representative compounds of the invention, when tested in one of the above reported protocols, displayed an $IC_{50}$ lower than 100 nM.

Representative compounds of the invention displayed an $IC_{50}$ lower than 100 nM in both PDE4 cell free and M3 binding assays.

The invention claimed is:

1. A compound, which is selected from the group consisting of:
[(1S)-2-(3,5-dichloro-1-oxido-pyridin-1-ium-4-yl)-1-(3,4-dimethoxyphenyl)ethyl] 4-[(3-cyano-5-hydroxy-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl] 4-[(3-hydroxy-5-methyl-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl] 4-[(2,6-dihydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl] 4-[(2-fluoro-3-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl] 4-[3-(N-[(3R)-quinuclidin-3-yl]oxycarbonylanilino)propyl]benzoate;

[(1S)-2-(3,5-dichloro-1-oxido-pyridin-1-ium-4-yl)-1-(3,4-dimethoxyphenyl)ethyl] 3-[(2-hydroxy-5-methoxy-N-[(3R)-quinuclidin-3-yl]oxycarbonyl-anilino)-methyl]benzoate;

[(1S)-2-(3,5-dichloro-1-oxido-pyridin-1-ium-4-yl)-1-(3,4-dimethoxyphenyl)ethyl] 3-[[2-(difluoromethyl)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl) ethyl]-4-[[2-(dimethylaminomethyl)-N-[(3R)-quinuclidin-3-yl]oxycarbonyl-anilino]methyl]benzoate; and

[(1S)-2-(3,5-dichloro-1-oxido-pyridin-1-ium-4-yl)-1-(3,4-dimethoxyphenyl)ethyl] 4-[3-(2-fluoro-N-[(3R)-quinuclidin-3-yl]oxycarbonyl-anilino)propyl]benzoate, or a pharmaceutically acceptable salt of said compound.

2. A pharmaceutical composition comprising a compound or pharmaceutically acceptable salt according to claim 1, either alone or in combination with another active ingredient, in admixture with one or more pharmaceutically acceptable carrier.

3. A method of treating a disease of the respiratory tract characterized by airway obstruction, comprising administering a compound or pharmaceutically acceptable salt according to claim 1 to a subject in need thereof.

4. A method according to claim 3 wherein the disease of the respiratory tract is selected from asthma and COPD.

5. An inhalation device comprising a pharmaceutical composition according to claim 2.

6. A kit comprising the pharmaceutical composition of claim 2 and a device which may be a single- or multi-dose dry powder inhaler, a metered dose inhaler or a nebulizer.

* * * * *